United States Patent
Champion et al.

(10) Patent No.: US 10,946,032 B2
(45) Date of Patent: *Mar. 16, 2021

(54) MIXTURES OF HMOS

(71) Applicant: Glycom A/S, Hørsholm (DK)

(72) Inventors: Elise Champion, Toulouse (FR); Bruce McConnell, La Tour de Peilz (CH); Gyula Dekany, Sinnamon Park (AU)

(73) Assignee: GLYCOM A/S, Hørsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/435,949

(22) Filed: Jun. 10, 2019

(65) Prior Publication Data

US 2019/0290667 A1 Sep. 26, 2019

Related U.S. Application Data

(63) Continuation of application No. 15/521,582, filed as application No. PCT/IB2015/058198 on Oct. 23, 2015, now Pat. No. 10,314,852.

(30) Foreign Application Priority Data

| Oct. 24, 2014 | (EP) | 14190374 |
|---|---|---|
| Feb. 17, 2015 | (EP) | 15155450 |
| Feb. 17, 2015 | (EP) | 15155454 |
| Feb. 17, 2015 | (EP) | 15155457 |
| Feb. 17, 2015 | (EP) | 15155460 |
| Apr. 9, 2015 | (EP) | 15163044 |
| Apr. 9, 2015 | (EP) | 15163045 |
| Apr. 9, 2015 | (EP) | 15163047 |

(51) Int. Cl.
*A61K 31/702* (2006.01)
*C07H 5/06* (2006.01)
*C12P 19/26* (2006.01)
*A61K 31/715* (2006.01)
*C12P 19/18* (2006.01)
*A61K 31/7016* (2006.01)

(52) U.S. Cl.
CPC ........ *A61K 31/702* (2013.01); *A61K 31/7016* (2013.01); *A61K 31/715* (2013.01); *C07H 5/06* (2013.01); *C12P 19/18* (2013.01); *C12P 19/26* (2013.01); *C12Y 204/01065* (2013.01)

(58) Field of Classification Search
None
See application file for complete search history.

(56) References Cited

U.S. PATENT DOCUMENTS

| 8,361,756 B2 | 1/2013 | Mills et al. | |
| 10,314,852 B2 * | 6/2019 | Champion | A61K 31/7016 |
| 2018/0169122 A1 * | 6/2018 | Hennet | A23C 9/206 |

FOREIGN PATENT DOCUMENTS

| EP | 0577580 A2 | 1/1994 |
|---|---|---|
| EP | 2522232 A1 | 11/2012 |
| EP | 2656862 A1 | 10/2013 |
| WO | 0104341 A1 | 1/2001 |
| WO | 2007101862 A1 | 9/2007 |
| WO | 2010115934 A1 | 10/2010 |
| WO | 2010115935 A1 | 10/2010 |
| WO | 2011100979 A1 | 8/2011 |
| WO | 2011100980 A1 | 8/2011 |
| WO | 2012112777 A2 | 8/2012 |
| WO | 2012155916 A1 | 11/2012 |
| WO | 2012156897 A1 | 11/2012 |
| WO | 2012156898 A1 | 11/2012 |
| WO | 2012158517 A1 | 11/2012 |
| WO | 2013025104 A1 | 2/2013 |
| WO | 2013044928 A1 | 4/2013 |
| WO | 2013091660 A1 | 6/2013 |
| WO | 2013139344 A1 | 9/2013 |
| WO | 2013154725 A1 | 10/2013 |

(Continued)

OTHER PUBLICATIONS

Klindworth, A. et al., "Evaluation of general 16S ribosomal RNA gene PCR primers for classical and next-generation sequencing-based diversity studies," Nucleic Acids Research, 2013, vol. 41(1), pp. 1-11. doi:10.1093/nar/gks808.

(Continued)

*Primary Examiner* — Eric Olson
(74) *Attorney, Agent, or Firm* — Neal, Gerber & Eisenberg LLP

(57) ABSTRACT

The invention relates to a mixture of human milk oligosaccharides that consists essentially of:
 a) a component A which is 3-FL or DFL,
  a component B which is LNT, LNnT, LNFP-I or 2'-FL,
  a component C, which is
   LNFP-II when component B is LNT, or
   LNFP-III when component B is LNnT, or
   LNDFH-I when component B is LNFP-I, or
   DFL when component B is 2'-FL, and
  a component D, which is
   lactose when component A is 3-FL, or
   2'-FL when component A is DFL,
  with the proviso that if component B is 2'-FL, then component A is 3-FL;
or consists essentially of:
 b) 3-FL,
  a component E which is LNT, LNnT or LNFP-I, and
  a component F, which is
   LNFP-II when component E is LNT, or
   LNFP-III when component E is LNnT, or
   LNDFH-I when component E is LNFP-I,
and to processes for producing them and their uses.

20 Claims, No Drawings
Specification includes a Sequence Listing.

(56) References Cited

FOREIGN PATENT DOCUMENTS

WO 2013190530 A1 12/2013
WO 2015071403 A1 5/2015

OTHER PUBLICATIONS

Kunz, C. et al.: "Bioactivity of buman milk oligosaccbarides." Food Oligos Accharides: Production, Analysis and Bioactivity, 2014, pp. 1-20.
Saumonneau, A. et al., "Design of an a-L-transfucosidase for the synthesis of fucosylated HMOs," Glycobiology, 2016, vol. 26(3), pp. 261-269.

* cited by examiner

```
                            SEQUENCE LISTING

<160> NUMBER OF SEQ ID NOS: 1

<210> SEQ ID NO 1
<211> LENGTH: 478
<212> TYPE: PRT
<213> ORGANISM: Bifidobacterium longum subsp. infantis

<400> SEQUENCE: 1

Met Asn Asn Pro Ala Asp Ala Gly Ile Asn Leu Asn Tyr Leu Ala Asn
1               5                   10                  15

Val Arg Pro Ser Ser Arg Gln Leu Ala Trp Gln Arg Met Glu Met Tyr
            20                  25                  30

Ala Phe Leu His Phe Gly Met Asn Thr Met Thr Asp Arg Glu Trp Gly
        35                  40                  45

Leu Gly His Glu Asp Pro Ala Leu Phe Asn Pro Arg Asn Val Asp Val
    50                  55                  60

Asp Gln Trp Met Asp Ala Leu Val Ala Gly Met Ala Gly Val Ile
65                  70                  75                  80

Leu Thr Cys Lys His His Asp Gly Phe Cys Leu Trp Pro Ser Arg Leu
                85                  90                  95

Thr Arg His Thr Val Ala Ser Ser Pro Trp Arg Glu Gly Lys Gly Asp
            100                 105                 110

Leu Val Arg Glu Val Ser Glu Ser Ala Arg Arg His Gly Leu Lys Phe
            115                 120                 125

Gly Val Tyr Leu Ser Pro Trp Asp Arg Thr Glu Glu Ser Tyr Gly Lys
        130                 135                 140

Gly Lys Ala Tyr Asp Asp Phe Tyr Val Gly Gln Leu Thr Glu Leu Leu
145                 150                 155                 160

Thr Gln Tyr Gly Pro Ile Phe Ser Val Trp Leu Asp Gly Ala Asn Gly
                165                 170                 175

Glu Gly Lys Asn Gly Lys Thr Gln Tyr Tyr Asp Trp Asp Arg Tyr Tyr
            180                 185                 190

Asn Val Ile Arg Ser Leu Gln Pro Asp Ala Val Ile Ser Val Cys Gly
            195                 200                 205

Pro Asp Val Arg Trp Ala Gly Asn Glu Ala Gly His Val Arg Asp Asn
        210                 215                 220

Glu Trp Ser Val Val Pro Arg Arg Leu Arg Ser Ala Glu Leu Thr Met
225                 230                 235                 240

Glu Lys Ser Gln Gln Glu Asp Asp Ala Ser Phe Ala Thr Val Ser
                245                 250                 255

Ser Gln Asp Asp Asp Leu Gly Ser Arg Glu Ala Val Ala Gly Tyr Gly
            260                 265                 270
```

-continued

```
Asp Asn Val Cys Trp Tyr Pro Ala Glu Val Asp Thr Ser Ile Arg Pro
    275                 280                 285

Gly Trp Phe Tyr His Gln Ser Glu Asp Asp Lys Val Met Ser Ala Asp
    290                 295                 300

Gln Leu Phe Asp Leu Trp Leu Ser Ala Val Gly Gly Asn Ser Ser Leu
305                 310                 315                 320

Leu Leu Asn Ile Pro Pro Ser Pro Glu Gly Leu Leu Ala Glu Pro Asp
                325                 330                 335

Val Gln Ser Leu Lys Gly Leu Gly Arg Arg Val Ser Glu Phe Arg Glu
                340                 345                 350

Ala Leu Ala Ser Val Arg Cys Glu Ala Arg Thr Ser Ser Ala Ser Ala
                355                 360                 365

Ala Ala Ala His Leu Val Asp Gly Asn Arg Asp Thr Phe Trp Arg Pro
    370                 375                 380

Asp Ala Asp Asp Ala Ala Pro Ala Ile Thr Leu Thr Leu Pro Gln Pro
385                 390                 395                 400

Thr Thr Ile Asn Ala Ile Val Ile Glu Glu Ala Ile Glu His Gly Gln
                405                 410                 415

Arg Ile Glu His Leu Arg Val Thr Gly Ala Leu Pro Asp Gly Thr Glu
            420                 425                 430

Arg Val Leu Gly Gln Ala Gly Thr Val Gly Tyr Arg Arg Ile Leu Arg
        435                 440                 445

Phe Asp Asp Val Glu Val Ser Ser Val Thr Leu His Val Asp Gly Ser
    450                 455                 460

Arg Leu Ala Pro Met Ile Ser Arg Ala Ala Ala Val Arg Ile
465                 470                 475
```

MIXTURES OF HMOS

CROSS-REFERENCE TO RELATED APPLICATIONS

This application is a continuation of U.S. patent application Ser. No. 15/521,582, filed Apr. 24, 2017, now U.S. Pat. No. 10,314,852, which is a national stage entry pursuant to 35 U.S.C. § 371 of International Patent Application No. PCT/IB2015/058198, filed on Oct. 23, 2015, which claims priority to European Patent Application No. 14190374.0, filed Oct. 24, 2014, European Patent Application No. 15155450.8, filed Feb. 17, 2015, European Patent Application No. 15155454.0, filed Feb. 17, 2015, European Patent Application No. 15155457.3, filed Feb. 17, 2015, European Patent Application No. 15155460.7, filed Feb. 17, 2015, European Patent Application No. 15163044.9, filed Apr. 9, 2015, European Patent Application No. 15163045.6, filed Apr. 9, 2015, European Patent Application No. 15163047.2, filed Apr. 9, 2015, the contents of all of which are fully incorporated herein by reference.

FIELD OF THE INVENTION

The present invention relates to mixtures of Human Milk Oligosaccharides ("HMOs"), a process for making the mixtures, and applications of the mixtures in human health.

BACKGROUND OF THE INVENTION

HMOs have become the subject of much interest in recent years due to their roles in numerous biological processes occurring in the human organism. Mammalian milk contains at least 130 of these complex oligosaccharides (Urashima et al, Milk Oligosaccharides, Nova Biomedical Books, New York, 2011, ISBN: 978-1-61122-831-1).

Previously, the only source of HMOs had been mammalian milk which contains mostly water, together with 55-70 g/l lactose, 24-59 g/l lipids, ca. 13 g/l proteins, 5-15 g/l HMOs and ca. 1.5 g/l minerals.

However, efforts to develop processes for synthesizing these oligosaccharides have increased significantly in the last ten years due to their roles in numerous human biological processes. In this regard, processes have been developed for producing HMOs by microbial fermentations, enzymatic processes, chemical syntheses, or combinations of these technologies. For example, by chemical processes, LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, and 6'-SL and salts thereof can be made as described in WO 2010/100979. As examples of biotechnological processes, WO 01/04341 and WO 2007/101862 describe how to make core human milk oligosaccharides optionally substituted by fucose or sialic acid using genetically modified E. coli. WO 2012/158517 and WO 2013/154725 describe prebiotic compositions containing 3-FL, 2'-FL and DFL and WO 2012/112777 describes a mixture of 3-FL, 2'-FL, DFL and lactose produced in a genetically modified E. coli. As an example of enzymatic processes, sialylated oligosaccharides can be made as described in EP-A-577580.

Efforts have also been made to develop processes for synthesizing enzymatically mixtures of HMO oligosaccharides, without having to synthesize all of the component oligosaccharides of the mixture as described in WO 2012/156897 and WO 2012/156898. Such processes have provided reaction mixtures containing a plurality of different oligosaccharides.

However, better processes have been sought for the synthesis of mixtures of HMOs.

Evidence is accumulating that the resident community of microbes, called the microbiome, in the human digestive tract plays a major role in health and disease. When the normal composition of the microbiome is thrown off balance, the human host can suffer consequences. Recent research has implicated microbiome imbalances in disorders as diverse as cancer, obesity, inflammatory bowel disease, psoriasis, asthma, and possibly even autism. HMOs are believed to positively modulate the microbiome, and they are of increasing interest for this purpose. However, the remarkable diversity of HMOs, coupled with their lack of availability, has hampered studies of the specific functions of individual HMOs. There is a clear need for specific HMOs or combinations of HMOs to modulate the microbiome in a desired manner, so as to address specific human health issues.

SUMMARY OF THE INVENTION

A first aspect of this invention relates to a mixture of HMOs consisting essentially of
  a component A which is 3-FL or DFL,
  a component B which is LNT, LNnT, LNFP-I or 2'-FL,
  a component C, which is:
    LNFP-II when component B is LNT, or
    LNFP-III when component B is LNnT, or
    LNDFH-I when component B is LNFP-I, or
    DFL when component B is 2'-FL, and
  a component D, which is:
    lactose when component A is 3-FL, or
    2'-FL when component A is DFL,
with the proviso that if component B is 2'-FL then component A is 3-FL. Preferably in the HMO mixture of the first aspect, component A is DFL.

A second aspect of this invention relates to a mixture of HMOs consisting essentially of
  3-FL,
  a component E which is LNT, LNnT or LNFP-I, and
  a component F, which is:
    LNFP-II when component E is LNT, or
    LNFP-III when component E is LNnT, or
    LNDFH-I when component E is LNFP-I.

A third aspect of this invention relates to a process for making a mixture of HMOs according to the first aspect, by reacting a component A and a component B in the presence of an α1-3/4 transfucosidase to produce a reaction mixture containing the components A, B, C and D, and then removing the α1-3/4 transfucosidase from the reaction mixture.

A fourth aspect of this invention relates to a process for obtaining a mixture of HMOs consisting essentially of:
  3-FL,
  a component B which is LNT, LNnT, LNFP-I or 2'-FL, and
  a component C, which is
    LNFP-II when component C is LNT, or
    LNFP-III when component C is LNnT, or
    LNDFH-I when component C is LNFP-I, or
    DFL when component C is 2'-FL,
preferably a mixture of the second aspect, comprising the steps of reacting 3-FL and a component B in the presence of an α1-3/4 transfucosidase to produce a reaction mixture containing 3-FL, lactose and the components B and C, and then removing lactose and the α1-3/4 transfucosidase from the reaction mixture.

A fifth aspect of this invention relates to an anti-infective composition for treating bacterial infections. The composition comprises, preferably consists essentially of:
DFL,
a component E which is LNT, LNnT or LNFP-I,
a component F, which is:
LNFP-II when component E is LNT, or
LNFP-III when component E is LNnT, or
LNDFH-I when component E is LNFP-I, and
2'-FL,
or
3-FL,
a component B which is LNT, LNnT, LNFP-I or 2'-FL, and
a component C, which is:
LNFP-II when component B is LNT, or
LNFP-III when component B is LNnT, or
LNDFH-I when component B is LNFP-I, or
DFL when component B is 2'-FL;
or the composition consists essentially of:
3-FL,
a component B which is LNT, LNnT, LNFP-I or 2'-FL,
a component C, which is:
LNFP-II when component B is LNT, or
LNFP-III when component B is LNnT, or
LNDFH-I when component B is LNFP-I, or
DFL when component B is 2'-FL, and
lactose.

Each of these anti-infective compositions contains a plurality of different HMOs with novel combinations of properties and biological activities. Specifically, each composition can increase *Bifidobacterium* abundance and *Barnesiella* abundance in the microbiome of a human. Preferably, each composition can reduce *Firmicutes* abundance in the human microbiome, especially *Clostridia*. Each composition can also be used to treat and/or reduce the risk of a broad range of bacterial infections of a human.

A sixth aspect of this invention relates to a method of modulating the microbiome of a human to increase *Bifidobacterium* abundance and *Barnesiella* abundance, preferably by reducing *Firmicutes* abundance, especially *Clostridia*.

A seventh aspect of this invention relates to a method of preventing or treating bacterial infections in a human, especially antibiotic resistant bacterial infections.

The methods of the sixth and seventh aspects each comprise administering, to the human:
i) a composition comprising, preferably consisting essentially of:
3-FL,
a component B which is LNT, LNnT, LNFP-I or 2'-FL, and
a component C, which is
LNFP-II when component B is LNT, or
LNFP-III when component B is LNnT, or
LNDFH-I when component B is LNFP-I, or
DFL when component B is 2'-FL;
or
ii) a composition consisting essentially of:
3-FL,
a component B which is LNT, LNnT, LNFP-I or 2'-FL, and
a component C, which is
LNFP-II when component B is LNT, or
LNFP-III when component B is LNnT, or
LNDFH-I when component B is LNFP-I, or
DFL when component B is 2'-FL; and
lactose;
or iii) a composition comprising, preferably consisting essentially of,
DFL,
a component E which is LNT, LNnT or LNFP-I,
a fucosylated component F, which is
LNFP-II when component E is LNT, or
LNFP-III when component E is LNnT, or
LNDFH-I when component E is LNFP-I, and
2'-FL.

DETAILED DESCRIPTION OF THE INVENTION

In accordance with this invention, it has been surprisingly discovered that mixture of HMOs can provide an anti-infective composition for treating bacterial infections through specific modulation of the microbiome. The mixture increases *Bifidobacterium* abundance and *Barnesiella* abundance of the microbiome. The mixture also reduces *Firmicutes* abundance of the microbiome; especially *Clostridia*. Humans having increased abundance of *Bifidobacterium* and *Barnesiella* in their microbiome are more resistant to a broad range of infections and recover more quickly from these infections, including from antibiotic resistant infections. It is believed that this improved resistance is attributable to the changes in the microbiome. The reduction in *Firmicutes* in the microbiome especially *Clostridia*, attributable to this mixture, imparts additional health benefits.

The First Aspect of the Invention

The first aspect is a mixture of HMOs consisting essentially of
a component A which is 3-FL or DFL,
a component B which is LNT, LNnT, LNFP-I or 2'-FL,
a component C, which is
LNFP-II when component B is LNT, or
LNFP-III when component B is LNnT, or
LNDFH-I when component B is LNFP-I, or
DFL when component B is 2'-FL, and
a component D, which is
lactose when component A is 3-FL, or
2'-FL when component A is DFL,
with the proviso that if component B is 2'-FL then component A is 3-FL.

In a preferred embodiment of the mixture of this first aspect, component A is 3-FL. More preferably the molar ratio of (3-FL+component B) relative to the component C is 0.8-9.50, and the molar ratio of lactose to the component C is about 1. Even more preferably, the molar ratio of 3-FL to the component B is 0.07-7.7. Particularly in a mixture consisting essentially of 3-FL, 2'-FL, DFL and lactose, the molar ratio of 3-FL to 2'-FL is 0.05-7.7.

In a further preferred embodiment of the mixture of this first aspect, component A is 3-FL and component B is LNT or LNnT. Preferably, one of the molar ratios of 3-FL to the component C and the component B to the component C is not more than 2.

According to this first aspect, especially preferred are:
i) a mixture of HMOs which consists essentially of 3-FL, LNT, LNFP-II and lactose and in which:
the molar ratio of (3-FL+LNT) relative to LNFP-I1 is 0.8-9.5, and the molar ratio of lactose relative to LNFP-I1 is about 1, provided that one of the molar ratios 3-FL to LNFP-II and LNT to LNFP-I1 is not more than 2; and ii) a mixture of HMOs which consists essentially of 3-FL, LNnT, LNFP-III and lactose, and in which:
the molar ratio of (3-FL+LNnT) relative to LNFP-III is 0.8-9.5, and
the molar ratio of lactose relative to LNFP-III is about 1, provided that one of the molar ratios 3-FL to LNFP-III and LNnT to LNFP-III is not more than 2.

In a further preferred embodiment of the mixture of the first aspect, component A is 3-FL and component B is LNFP-I or 2'-FL. Preferably, one of the molar ratios of 3-FL to the component C and of the component B to the component C is not more than 2, and/or the molar ratio of 3-FL to the component B is 0.07-7.7.

Especially preferred is a mixture of HMOs which consists essentially of 3-FL, LNFP-I, LNDFH-I and lactose. Preferably, in this HMO mixture:
the molar ratio of (3-FL+LNFP-I) relative to LNDFH-I is 0.8-9.5, and
the molar ratio of lactose relative to LNDFH-I is about 1;
and more preferably in this mixture:
one of the molar ratios of 3-FL to LNDFH-I and LNFP-I to LNDFH-I is not more than 2.

Also according to this first aspect, especially preferred is a mixture of HMOs which consists essentially of 3-FL, 2'-FL, DFL and lactose. Preferably, in this mixture:
the molar ratio of (3-FL+2'-FL) relative to DFL is 0.8-9.5 and
the molar ratio of lactose relative to DFL is about 1.
More preferably, this mixture has a molar ratio of 3-FL to 2'-FL of 0.05-7.7 or 0.07-7.7. Also more preferably, the molar ratio of 3-FL to DFL or of 2'-FL to DFL is not more than 2.

In still another preferred embodiment of the mixture of the first aspect, component A is DFL. Preferably, the molar ratio of the component C relative to (DFL+component B) is at least 1:10, preferably at least 1:7, more preferably at least 1:5, even more preferably at least 1:3. Also preferably, the molar ratio of DFL relative to the component B is 0.17-6, preferably 0.25-4, more preferably about 1.

The mixture of this first aspect can consist essentially of 2'-FL, DFL, LNT and LNFP-II. This HMO mixture preferably has a molar ratio of LNFP-II relative to (DFL+LNT) of at least 1:10, more preferably at least 1:7, even more preferably at least 1:5, especially 1:3. This HMO mixture also preferably has a molar ratio of DFL relative to LNT of 0.17-6, preferably 0.25-4, more preferably about 1. Also preferably, this mixture has a molar ratio of 2'-FL relative to LNFP-II of about 1.

The mixture of the first aspect can also consist essentially of 2'-FL, DFL, LNnT and LNFP-III. This HMO mixture preferably has a molar ratio of LNFP-III relative to (DFL+LNnT) of at least 1:10, more preferably at least 1:7, even more preferably at least 1:5, especially 1:3. This HMO mixture also preferably has a molar ratio of DFL relative to LNnT of 0.17-6, preferably 0.25-4, more preferably about 1. Also preferably, this mixture has a molar ratio of 2'-FL relative to LNFP-III of about 1.

The mixture of the first aspect can also consist essentially of 2'-FL, DFL, LNFP-I and LNDFH-I. This HMO mixture preferably has a molar ratio of LNDFH-I relative to (DFL+LNFP-I) of at least 1:10, more preferably at least 1:7, even more preferably at least 1:5, especially 1:3. This HMO mixture also preferably has a molar ratio of DFL relative to LNFP-I of 0.17-6, preferably 0.25-4, more preferably about 1. Also preferably, this mixture has a molar ratio of 2'-FL relative to LNDFH-I of about 1.

The Second Aspect of the Invention

The second aspect is a mixture of HMOs consisting essentially of
3-FL,
a component E which is LNT, LNnT or LNFP-I, and
a component F which is
LNFP-II when component E is LNT, or
LNFP-III when component E is LNnT, or
LNDFH-I when component E is LNFP-I.

Preferably, the molar ratio of the component F relative to (3-FL+component E) is at least 1:10, preferably at least 1:7, more preferably at least 1:5, even more preferably at least 1:3, and/or the molar ratio of 3-FL relative to the component E is 0.05-21, preferably 0.13-7.7, more preferably about 1.

The mixture of the second aspect can consist essentially of 3-FL, LNT and LNFP-II. This HMO mixture preferably has a molar ratio of LNFP-II relative to (3-FL+LNT) of at least 1:10, more preferably at least 1:7, even more preferably at least 1:5, especially 1:3. This HMO mixture also preferably has a molar ratio of 3-FL relative to LNT of 0.05-21, preferably 0.13-7.7, more preferably about 1.

The mixture of the second aspect also can consist essentially of 3-FL, LNnT and LNFP-III. This HMO mixture preferably has a molar ratio of LNFP-III relative to (3-FL+LNnT) of at least 1:10, more preferably at least 1:7, even more preferably at least 1:5, especially 1:3. This HMO mixture also preferably has a molar ratio of 3-FL relative to LNnT of 0.05-21, preferably 0.13-7.7, more preferably about 1.

The mixture of the second aspect can also consist essentially of 3-FL, LNFP-I and LNDFH-I. This HMO mixture preferably has a molar ratio of LNDFH-I relative to (3-FL+LNFP-I) of at least 1:10, more preferably at least 1:7, even more preferably at least 1:5, especially 1:3. This HMO mixture also preferably has a molar ratio of 3-FL relative to LNFP-I of 0.05-21, preferably 0.13-7.7, more preferably about 1.

The Third Aspect of the Invention

The third aspect is a process for obtaining a mixture of the first aspect of the invention, including its preferred and the more preferred embodiments, comprising the steps of reacting a component A and a component B in the presence of an α1-3/4 transfucosidase to produce a reaction mixture containing the components A, B, C and D, and then removing the α1-3/4 transfucosidase from the reaction mixture. The α1-3/4 transfucosidase can be removed in a conventional manner, e.g., by denaturing the reaction mixture followed by its centrifugation or ultrafiltration.

In carrying out a process of the third aspect this invention, particular relative concentrations of the component A donor, component B acceptor, the α1-3/4 transfucosidase, the aqueous solvent and the incubation buffer (e.g. 50 mM $Na_3PO_4$ or 100 mM $KHPO_4$) are not critical. In this regard, the process can be suitably carried out at room temperature (e.g. 15-50, preferably 20-37° C.) at a pH of 6-8, preferably 6.5-7 for 15 min to 24 hours.

The Process of the Third Aspect, Carried Out with DFL as the Component A

This process involves reacting DFL as a donor and a component B as an acceptor in a molar ratio of 1:5 to 5:1, preferably 1:3 to 3:1, more preferably 1:2 to 2:1, even more preferably 1:1, in the presence of an α1-3/4 transfucosidase having a conversion rate of at least 10%, up to about 60%, preferably at least 20%, more preferably at least 30%, for the reaction of DFL and the component B.

An HMO mixture of this invention can be readily obtained by this process by treating DFL and LNT with an α1-3/4 transfucosidase to produce a reaction mixture and then removing the α1-3/4 transfucosidase from the reaction mixture. This process preferably comprises the step of contacting DFL and LNT in a molar ratio of preferably 1:5 to 5:1, more preferably 1:3 to 3:1, even more preferably 1:2 to 2:1, yet even more preferably 1:1, with an α1-3/4 transfucosidase having a conversion rate of at least 10%, up to about 60%, preferably at least 15%, more preferably at least 20%, even more preferably at least 25 To, yet more preferably at least 30%, for the reaction of DFL with LNT. The reaction mixture, so-produced, containing LNFP-II, 2'-FL, unreacted DFL, LNT and α1-3/4 transfucosidase, is then subjected to conventional purification steps to remove the α1-3/4 transfucosidase. The α1-3/4 transfucosidase can be removed, e.g., by denaturing it followed by centrifugation or ultrafiltration to produce a mixture consisting essentially of DFL, LNT, LNFP-II and 2'-FL. In the following statements beginning "When the process [ . . . ] is carried out . . . ", the expression "can be made" is equivalent to the expression "is obtained".

When the process of this invention is carried out with a molar ratio of DFL to LNT of 2:1 to 1:2 and a conversion rate of 20-50%, an HMO mixture having a molar ratio of (DFL+LNT) to LNFP-II of 2-13 and a molar ratio of DFL to LNT of 0.33-6 can be made. When the process is carried out with a molar ratio of DFL to LNT of 1:1 and a conversion rate of 20-50%, an HMO mixture having a molar ratio of (DFL+LNT) to LNFP-I1 of 2-8 and a molar ratio of DFL to LNT of 1 can be made.

When the process is carried out with a molar ratio of DFL to LNT of 3:1 to 1:3 and a conversion rate of 30-50%, an HMO mixture having a molar ratio of (DFL+LNT) to LNFP-I1 of 2-12 and a molar ratio of DFL to LNT of 0.2-5 can be made.

When the process is carried out with a molar ratio of DFL to LNT of 2:1 to 1:2 and a conversion rate of 30-50%, an HMO mixture having a molar ratio of (DFL+LNT) to LNFP-I1 of 2-8 and a molar ratio of DFL to LNT of 0.33-3 can be made.

When the process is carried out with a molar ratio of DFL to LNT of 1:1 and a conversion rate of 30-50%, an HMO mixture having a molar ratio of (DFL+LNT) to LNFP-I1 of 2-4.67 and a molar ratio of DFL to LNT of 1 can be made.

When the process is carried out with a molar ratio of DFL to LNT of 3:1 to 1:3 and a conversion rate of 20-40%, an HMO mixture having a molar ratio of (DFL+LNT) to LNFP-I1 of 3-18 and a molar ratio of DFL to LNT of 0.23-4.33 can be made.

When the process is carried out with a molar ratio of DFL to LNT of 2:1 to 1:2 and a conversion rate of 20-40%, an HMO mixture having a molar ratio of (DFL+LNT) to LNFP-II of 3-13 and a molar ratio of DFL to LNT of 0.38-2.67 can be made.

When the process is carried out with a molar ratio of DFL to LNT of 1:1 and a conversion rate of 20-40%, an HMO mixture having a molar ratio of (DFL+LNT) to LNFP-I1 of 3-8 and a molar ratio of DFL to LNT of 1 can be made.

When the process is carried out with a molar ratio of DFL to LNT of 3:1 to 2:1 and a conversion rate of 30-50%, an HMO mixture having a molar ratio of (DFL+LNT) to LNFP-I1 of 4-11.3 and a molar ratio of DFL to LNT of 2.5-5 can be made.

When the process is carried out with a molar ratio of DFL to LNT of 2:1 to 1:1 and a conversion rate of 20-40%, an HMO mixture having a molar ratio of (DFL+LNT) to LNFP-I1 of 3-13 and a molar ratio of DFL to LNT of 1-2.67 can be made.

When the process is carried out with a molar ratio of DFL to LNT of 1:1 to 1:2 and a conversion rate of 20-40%, an HMO mixture having a molar ratio of (DFL+LNT) to LNFP-I1 of 3-13 and a molar ratio of DFL to LNT of 0.38-1 can be made.

When the process is carried out with a molar ratio of DFL to LNT of 1:2 to 1:3 and a conversion rate of 30-50%, an HMO mixture having a molar ratio of (DFL+LNT) to LNFP-I1 of 4-11.3 and a molar ratio of DFL to LNT of 0.2-0.41 can be made.

An HMO mixture of this invention can also be readily obtained by this process by treating DFL donor and LNnT with an α1-3/4 transfucosidase to produce a reaction mixture and then removing the α1-3/4 transfucosidase from the reaction mixture. This process preferably comprises the step of contacting DFL and LNnT in a molar ratio of preferably 1:5 to 5:1, more preferably 1:3 to 3:1, even more preferably 1:2 to 2:1, yet even more preferably 1:1, with an α1-3/4 transfucosidase having a conversion rate of at least 10%, up to about 60%, preferably at least 15%, more preferably at least 20%, even more preferably at least 25%, yet more preferably at least 30%, for the reaction of DFL with LNnT. The reaction mixture, so-produced, containing LNFP-III, 2'-FL, unreacted DFL, LNnT and α1-3/4 transfucosidase, is then subjected to conventional purification steps to remove the α1-3/4 transfucosidase. The α1-3/4 transfucosidase can be removed, e.g., by denaturing it followed by centrifugation or ultrafiltration to produce a mixture consisting essentially of DFL, LNnT, LNFP-III and 2'-FL.

In the following statements beginning "When the process [ . . . ] is carried out . . . ", the expression "can be made" is equivalent to the expression "is obtained".

When the process of this invention is carried out with a molar ratio of DFL to LNnT of 2:1 to 1:2 and a conversion rate of 20-50%, an HMO mixture having a molar ratio of (DFL+LNnT) to LNFP-III of 2-13 and a molar ratio of DFL to LNnT of 0.33-6 can be made.

When the process is carried out with a molar ratio of DFL to LNnT of 1:1 and a conversion rate of 20-50%, an HMO mixture having a molar ratio of (DFL+LNnT) to LNFP-III of 2-8 and a molar ratio of DFL to LNnT of 1 can be made.

When the process is carried out with a molar ratio of DFL to LNnT of 3:1 to 1:3 and a conversion rate of 30-50%, an HMO mixture having a molar ratio of (DFL+LNnT) to LNFP-III of 2-12 and a molar ratio of DFL to LNnT of 0.2-5 can be made.

When the process is carried out with a molar ratio of DFL to LNnT of 2:1 to 1:2 and a conversion rate of 30-50%, an HMO mixture having a molar ratio of (DFL+LNnT) to LNFP-III of 2-8 and a molar ratio of DFL to LNnT of 0.33-3 can be made.

When the process is carried out with a molar ratio of DFL to LNnT of 1:1 and a conversion rate of 30-50%, an HMO mixture having a molar ratio of (DFL+LNnT) to LNFP-III of 2-4.67 and a molar ratio of DFL to LNnT of 1 can be made.

When the process is carried out with a molar ratio of DFL to LNnT of 3:1 to 1:3 and a conversion rate of 20-40%, an HMO mixture having a molar ratio of (DFL+LNnT) to LNFP-III of 3-18 and a molar ratio of DFL to LNnT of 0.23-4.33 can be made.

When the process is carried out with a molar ratio of DFL to LNnT of 2:1 to 1:2 and a conversion rate of 20-40%, an HMO mixture having a molar ratio of (DFL+LNnT) to LNFP-III of 3-13 and a molar ratio of DFL to LNnT of 0.38-2.67 can be made.

When the process is carried out with a molar ratio of DFL to LNnT of 1:1 and a conversion rate of 20-40%, an HMO mixture having a molar ratio of (DFL+LNnT) to LNFP-III of 3-8 and a molar ratio of DFL to LNnT of 1 can be made.

When the process is carried out with a molar ratio of DFL to LNnT of 3:1 to 2:1 and a conversion rate of 30-50%, an HMO mixture having a molar ratio of (DFL+LNnT) to LNFP-III of 4-11.3 and a molar ratio of DFL to LNnT of 2.5-5 can be made.

When the process is carried out with a molar ratio of DFL to LNnT of 2:1 to 1:1 and a conversion rate of 20-40%, an HMO mixture having a molar ratio of (DFL+LNnT) to LNFP-III of 3-13 and a molar ratio of DFL to LNnT of 1-2.67 can be made.

When the process is carried out with a molar ratio of DFL to LNnT of 1:1 to 1:2 and a conversion rate of 20-40%, an HMO mixture having a molar ratio of (DFL+LNnT) to LNFP-III of 3-13 and a molar ratio of DFL to LNnT of 0.38-1 can be made.

When the process is carried out with a molar ratio of DFL to LNnT of 1:2 to 1:3 and a conversion rate of 30-50%, an HMO mixture having a molar ratio of (DFL+LNnT) to LNFP-III of 4-11.3 and a molar ratio of DFL to LNnT of 0.2-0.41 can be made.

An HMO mixture of this invention can also be readily obtained by this process by treating DFL and LNFP-I with an α1-3/4 transfucosidase to produce a reaction mixture and then removing the α1-3/4 transfucosidase from the reaction mixture. This process preferably comprises the step of contacting DFL and LNFP-I in a molar ratio of preferably 1:5 to 5:1, more preferably 1:3 to 3:1, even more preferably 1:2 to 2:1, yet even more preferably 1:1, with an α1-3/4 transfucosidase having a conversion rate of at least 10%, up to about 60%, preferably at least 15%, more preferably at least 20%, even more preferably at least 25%, yet more preferably at least 30%, for the reaction of DFL with LNFP-I. The reaction mixture, so-produced, containing LNDFH-I, 2'-FL, unreacted DFL, LNFP-I and α1-3/4 transfucosidase, is then subjected to conventional purification steps to remove the α1-3/4 transfucosidase. The α1-3/4 transfucosidase can be removed, e.g., by denaturing it followed by centrifugation or ultrafiltration to produce a mixture consisting essentially of DFL, LNFP-I, LNDFH-I and 2'-FL.

In the following statements beginning "When the process [ . . . ] is carried out . . . ", the expression "can be made" is equivalent to the expression "is obtained".

When the process of this invention is carried out with a molar ratio of DFL to LNFP-I of 2:1 to 1:2 and a conversion rate of 20-50%, an HMO mixture having a molar ratio of (DFL+LNFP-I) to LNDFH-I of 2-13 and a molar ratio of DFL to LNFP-I of 0.33-6 can be made.

When the process is carried out with a molar ratio of DFL to LNFP-I of 1:1 and a conversion rate of 20-50%, an HMO mixture having a molar ratio of (DFL+LNFP-I) to LNDFH-I of 2-8 and a molar ratio of DFL to LNFP-I of 1 can be made.

When the process is carried out with a molar ratio of DFL to LNFP-I of 3:1 to 1:3 and a conversion rate of 30-50%, an HMO mixture having a molar ratio of (DFL+LNFP-I) to LNDFH-I of 2-12 and a molar ratio of DFL to LNFP-I of 0.2-5 can be made.

When the process is carried out with a molar ratio of DFL to LNFP-I of 2:1 to 1:2 and a conversion rate of 30-50%, an HMO mixture having a molar ratio of (DFL+LNFP-I) to LNDFH-I of 2-8 and a molar ratio of DFL to LNFP-I of 0.33-3 can be made.

When the process is carried out with a molar ratio of DFL to LNFP-I of 1:1 and a conversion rate of 30-50%, an HMO mixture having a molar ratio of (DFL+LNFP-I) to LNDFH-I of 2-4.67 and a molar ratio of DFL to LNFP-I of 1 can be made.

When the process is carried out with a molar ratio of DFL to LNFP-I of 3:1 to 1:3 and a conversion rate of 20-40%, an HMO mixture having a molar ratio of (DFL+LNFP-I) to LNDFH-I of 3-18 and a molar ratio of DFL to LNFP-I of 0.23-4.33 can be made.

When the process is carried out with a molar ratio of DFL to LNFP-I of 2:1 to 1:2 and a conversion rate of 20-40%, an HMO mixture having a molar ratio of (DFL+LNFP-I) to LNDFH-I of 3-13 and a molar ratio of DFL to LNFP-I of 0.38-2.67 can be made.

When the process is carried out with a molar ratio of DFL to LNFP-I of 1:1 and a conversion rate of 20-40%, an HMO mixture having a molar ratio of (DFL+LNFP-I) to LNDFH-I of 3-8 and a molar ratio of DFL to LNFP-I of 1 can be made.

When the process is carried out with a molar ratio of DFL to LNFP-I of 3:1 to 2:1 and a conversion rate of 30-50%, an HMO mixture having a molar ratio of (DFL+LNFP-I) to LNDFH-I of 4-11.3 and a molar ratio of DFL to LNFP-I of 2.5-5 can be made.

When the process is carried out with a molar ratio of DFL to LNFP-I of 2:1 to 1:1 and a conversion rate of 20-40%, an HMO mixture having a molar ratio of (DFL+LNFP-I) to LNDFH-I of 3-13 and a molar ratio of DFL to LNFP-I of 1-2.67 can be made.

When the process is carried out with a molar ratio of DFL to LNFP-I of 1:1 to 1:2 and a conversion rate of 20-40%, an HMO mixture having a molar ratio of (DFL+LNFP-I) to LNDFH-I of 3-13 and a molar ratio of DFL to LNFP-I of 0.38-1 can be made.

When the process is carried out with a molar ratio of DFL to LNFP-I of 1:2 to 1:3 and a conversion rate of 30-50%, an HMO mixture having a molar ratio of (DFL+LNFP-I) to LNDFH-I of 4-11.3 and a molar ratio of DFL to LNFP-I of 0.2-0.41 can be made.

The Process of the Third Aspect, Carried Out with 3-FL as the Component A

Alternatively, the process of the third aspect can be carried out with 3-FL as a donor and a component B as an acceptor in a molar ratio of 1:5 to 5:1, preferably 1:3 to 3:1, more preferably 1:2 to 2:1, even more preferably 1:1, in the presence of an α1-3/4 transfucosidase having a conversion rate of at least 35%, up to about 80%, preferably at least 40%, more preferably at least 50%, for the reaction of 3-FL and the component B. The reaction mixture, so-produced can then be subjected to conventional purification steps to remove the α1-3/4 transfucosidase. The α1-3/4 transfucosidase can be removed, e.g., by denaturing it followed by centrifugation or ultrafiltration.

In a preferred embodiment of the alternative process of the third aspect, an HMO mixture of this invention can be readily obtained by treating 3-FL and LNFP-I or 2'-FL with an α1-3/4 transfucosidase to produce a reaction mixture and then removing the α1-3/4 transfucosidase from the reaction mixture. This process preferably comprises the step of contacting 3-FL and LNFP-I or 2'-FL in a molar ratio of 1:3 to 3:1, preferably 1:2 to 2:1, more preferably 1:1, in the presence of an α1-3/4 transfucosidase having a conversion rate of at least 35%, up to about 70%, preferably at least 40%, more preferably at least 50%, for the reaction of 3-FL with LNFP-I or 2'-FL.

In a more preferred embodiment, an HMO mixture consisting essentially of 3-FL, LNFP-I, LNDFH-I and lactose can be readily obtained by treating 3-FL and LNFP-I in a molar ratio of preferably 1:5 to 5:1, more preferably 1:3 to 3:1, even more preferably 1:2 to 2:1, yet even more preferably 1:1, with an α1-3/4 transfucosidase having a conversion rate of at least 35%, up to about 70%, preferably at least 40%, more preferably at least 50%, for the reaction of 3-FL with LNFP-I.

In another more preferred embodiment, an HMO mixture consisting essentially of 3-FL, 2'-FL, DFL and lactose can be readily obtained by treating 3-FL and 2'-FL in a molar ratio of preferably 1:5 to 5:1, more preferably 1:3 to 3:1, even more preferably 1:2 to 2:1, yet even more preferably 1:1 with an α1-3/4 transfucosidase having a conversion rate of at least 10%, up to about 70%, preferably at least 20%, more preferably at least 35%, even more preferably at least 40%, yet more preferably at least 50%, for the reaction of 3-FL with 2'-FL.

In another preferred embodiment of the alternative process of the third aspect, an HMO mixture of this invention can be readily obtained by treating 3-FL and LNT or LNnT with an α1-3/4 transfucosidase to produce a reaction mixture and then the α1-3/4 transfucosidase is removed from the reaction mixture. This process preferably involves reacting 3-FL and LNT or LNnT in a molar ratio of 1:3 to 3:1, preferably 1:2 to 2:1, more preferably 1:1, in the presence of an α1-3/4 transfucosidase having a conversion rate of at least 35%, up to about 70%, preferably at least 40%, more preferably at least 50%, for the reaction of 3-FL with LNT or LNnT.

In a more preferred embodiment, an HMO mixture consisting essentially of 3-FL, LNT, LNFP-II and lactose, and in which:

the molar ratio of (3-FL+LNT) relative to LNFP-I1 is 0.8-9.5, and the molar ratio of lactose relative to LNFP-II is about 1, provided that one of the molar ratios 3-FL to LNFP-II and LNT to LNFP-I1 is not more than 2, can be readily obtained by treating 3-FL and LNT in a molar ratio of preferably 1:5 to 5:1, more preferably 1:3 to 3:1, even more preferably 1:2 to 2:1, yet even more preferably 1:1, and with an α1-3/4 transfucosidase having a conversion rate of at least 35%, up to about 70%, preferably at least 40%, more preferably at least 50% for the reaction of 3-FL with LNT.

In another more preferred embodiment, an HMO mixture consisting essentially of 3-FL, LNnT, LNFP-III and lactose, and in which:

the molar ratio of (3-FL+LNnT) relative to LNFP-III is 0.8-9.5, and the molar ratio of lactose relative to LNFP-III is about 1, provided that one of the molar ratios 3-FL to LNFP-III and LNnT to LNFP-III is not more than 2, can be obtained by treating 3-FL and LNnT in a molar ratio of preferably 1:5 to 5:1, more preferably 1:3 to 3:1, even more preferably 1:2 to 2:1, yet even more preferably 1:1, with an α1-3/4 transfucosidase having a conversion rate of at least 35%, up to about 70%, preferably at least 40%, more preferably at least 50% for the reaction of 3-FL with LNnT.

The Fourth Aspect of the Invention

The fourth aspect is a process for obtaining a mixture of HMOs consisting essentially of

3-FL, a component B which is LNT, LNnT, LNFP-I or 2'-FL, and a component C, which is:
LNFP-II when component B is LNT, or
LNFP-III when component B is LNnT, or
LNDFH-I when component B is LNFP-I, or
DFL when component B is 2'-FL, preferably a mixture of the second aspect, including its preferred and the more preferred embodiments, comprising the steps of reacting 3-FL as a donor and a component B as an acceptor in the presence of an α1-3/4 transfucosidase to produce a reaction mixture, and then removing lactose and the α1-3/4 transfucosidase from the reaction mixture. The α1-3/4 transfucosidase can be removed, e.g. by denaturing it followed by centrifugation or ultrafiltration. The lactose can be separated from the 3-FL, component B and component C, e.g. by cascade ultra- and/or nanofiltration, or the lactose can first be treated with lactase to degrade it to glucose and galactose which can then be separated from the 3-FL, component B and component C by ultra- and/or nanofiltration.

In carrying out a process of the fourth aspect of this invention, particular relative concentrations of the 3-FL donor, component B acceptor, the α1-3/4 transfucosidase, the aqueous solvent and the incubation buffer (e.g. 50 mM $Na_3PO_4$ or 100 mM $KHPO_4$) are not critical. In this regard, the process can be suitably carried out at room temperature (e.g. 15-50, preferably 20-37° C.) at a pH of 6-8, preferably 6.5-7 for 15 min to 24 hours.

The process preferably comprises the step of reacting 3-FL and the component B in a molar ratio of 1:5 to 5:1, preferably 1:3 to 3:1, more preferably 1:2 to 2:1, even more preferably 1:1, in the presence of an α1-3/4 transfucosidase having a conversion rate of at least 35%, up to about 80%, preferably at least 40%, more preferably at least 50%, for the reaction of 3-FL and a component B.

In a preferred embodiment of the process of the fourth aspect, an HMO mixture consisting essentially of 3-FL, LNT and LNFP-II can be readily obtained by treating 3-FL and LNT with an α1-3/4 transfucosidase to produce a reaction mixture and then removing lactose and the α1-3/4 transfucosidase from the reaction mixture as described above. This process preferably comprises the step of contacting 3-FL and LNT in a molar ratio of preferably 1:5 to 5:1, more preferably 1:3 to 3:1, even more preferably 1:2 to 2:1, yet even more preferably 1:1, with an α1-3/4 transfucosidase having a conversion rate of at least 10%, up to about 70%, preferably at least 20%, more preferably at least 35%, even more preferably at least 40%, yet more preferably at least 50%, for the reaction of 3-FL and LNT. From the reaction mixture, so-produced, containing LNFP-II, lactose, unreacted 3-FL, LNT and the α1-3/4 transfucosidase, the α1-3/4 transfucosidase and the lactose can then be removed as described above.

In another preferred embodiment of the process of the fourth aspect, an HMO mixture consisting essentially of 3-FL, LNnT and LNFP-III can be readily obtained by treating 3-FL and LNnT with an α1-3/4 transfucosidase to produce a reaction mixture and then removing lactose and the α1-3/4 transfucosidase from the reaction mixture as described above. This process preferably comprises the step of contacting 3-FL and LNnT in a molar ratio of 1:5 to 5:1, more preferably 1:3 to 3:1, even more preferably 1:2 to 2:1, yet even more preferably 1:1, with an α1-3/4 transfucosidase having a conversion rate of at least 10%, up to about 70%, preferably at least 20%, more preferably at least 35%, even more preferably at least 40%, yet more preferably at least 50%, for the reaction of 3-FL and LNnT. From the reaction mixture, so-produced, containing LNFP-III, lactose, unreacted 3-FL, LNnT and the α1-3/4 transfucosidase, α1-3/4 transfucosidase and the lactose can then be removed as described above.

In yet another preferred embodiment of the process of the fourth aspect, an HMO mixture consisting essentially of 3-FL, LNFP-I, LNDFH-I can be readily obtained by treating 3-FL and LNFP-I with an α1-3/4 transfucosidase to produce a reaction mixture and then removing lactose and the α1-3/4 transfucosidase from the reaction mixture as described above. This process preferably comprises the step of contacting 3-FL and LNFP-I in a molar ratio of preferably 1:5 to 5:1, more preferably 1:3 to 3:1, even more preferably 1:2 to 2:1, yet even more preferably 1:1, with an α1-3/4 transfucosidase having a conversion rate of at least 10%, up to about 70%, preferably at least 20%, more preferably at least 35%, even more preferably at least 40%, yet more preferably at least 50%, for the reaction of 3-FL and LNFP-I. From the reaction mixture, so-produced, containing LNDFH-I, lactose, unreacted 3-FL, LNFP-I and α1-3/4 transfucosidase, the α1-3/4 transfucosidase and the lactose can then be removed as described above.

In a further preferred embodiment of the process of the fourth aspect, an HMO mixture consisting essentially of 3-FL, 2'-FL and DFL can be readily obtained by treating 3-FL and 2'-FL acceptor, with an α1-3/4 transfucosidase to produce a reaction mixture containing DFL, lactose, unreacted 3-FL, 2'-FL and α1-3/4 transfucosidase. The mixture is then be subjected to conventional purification steps to remove the lactose and the α1-3/4 transfucosidase as described above. This HMO mixture so-obtained preferably has a molar ratio of DFL relative to (3-FL+2'-FL) of at least 1:10, more preferably at least 1:7, even more preferably at least 1:5, especially 1:3. This HMO mixture also has a molar ratio of 3-FL relative to 2'-FL of preferably 0.05-21, more preferably 0.13-7.7, even more preferably about 1.

Particularly Preferred Third and Fourth Aspects of the Invention

In the following statements beginning "When the process [ . . . ] is carried out . . . ", the expression "can be made" is equivalent to the expression "is obtained".

When a process of the third or the fourth aspect is carried out with a molar ratio of 3-FL to LNT of 2:1 to 1:2 and a conversion rate of 35-70%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 0.8-6.6 and a molar ratio of 3-FL to LNT of 0.2-4.5 can be made.

When a process of the third or the fourth aspect is carried out with a molar ratio of 3-FL to LNT of 1:1 and a conversion rate of 35-70%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 0.8-3.8 and a molar ratio of 3-FL to LNT of 1 can be made.

When a process of the third or the fourth aspect is carried out with a molar ratio of 3-FL to LNT of 3:1 to 1:3 and a conversion rate of 40-70%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 0.8-8 and a molar ratio of 3-FL to LNT of 0.13-7.7 can be made.

When a process of the third or the fourth aspect is carried out with a molar ratio of 3-FL to LNT of 2:1 to 1:2 and a conversion rate of 40-70%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 0.8-5.5 and a molar ratio of 3-FL to LNT of 0.2-4.5 can be made.

When a process of the third or the fourth aspect is carried out with a molar ratio of 3-FL to LNT of 1:1 and a conversion rate of 40-70%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 0.8-3 and a molar ratio of 3-FL to LNT of 1 can be made.

When a process of the third or the fourth aspect is carried out with a molar ratio of 3-FL to LNT of 3:1 to 1:3 and a conversion rate of 50-70%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 0.8-6 and a molar ratio of 3-FL to LNT of 0.13-7.7 can be made.

When a process of the third or the fourth aspect is carried out with a molar ratio of 3-FL to LNT of 2:1 to 1:2 and a conversion rate of 50-70%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 0.8-4 and a molar ratio of 3-FL to LNT of 0.2-4.5 can be made.

When a process of the third or the fourth aspect is carried out with a molar ratio of 3-FL to LNT of 1:1 and a conversion rate of 50-70%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 0.8-2 and a molar ratio of 3-FL to LNT of 1 can be made.

When a process of the third or the fourth aspect is carried out with a molar ratio of 3-FL to LNT of 3:1 to 1:3 and a conversion rate of 40-60%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 1.3-8 and a molar ratio of 3-FL to LNT of 0.17-6 can be made.

When a process of the third or the fourth aspect is carried out with a molar ratio of 3-FL to LNT of 2:1 to 1:2 and a conversion rate of 40-60%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 2-6.6 and a molar ratio of 3-FL to LNT of 0.25-3.5 can be made.

When a process of the third or the fourth aspect is carried out with a molar ratio of 3-FL to LNT of 1:1 and a conversion rate of 40-60%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 1.3-3 and a molar ratio of 3-FL to LNT of 1 can be made.

When a process of the third or the fourth aspect is carried out with a molar ratio of 3-FL to LNT of 5:1 to 3:1 and a conversion rate of 50-80%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 3-10 and a molar ratio of 3-FL to LNT of 5-21 can be made.

When a process of the third or the fourth aspect is carried out with a molar ratio of 3-FL to LNT of 3:1 to 2:1 and a conversion rate of 40-70%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 2-8 and a molar ratio of 3-FL to LNT of 2.5-7.7 can be made.

When a process of the third or the fourth aspect is carried out with a molar ratio of 3-FL to LNT of 2:1 to 1:1 and a conversion rate of 35-55%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 1.6-6.6 and a molar ratio of 3-FL to LNT of 1-3.3 can be made.

When a process of the third or the fourth aspect is carried out with a molar ratio of 3-FL to LNT of 1:1 to 1:2 and a conversion rate of 35-55%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 1.6-6.6 and a molar ratio of 3-FL to LNT of 0.3-1 can be made.

When a process of the third or the fourth aspect is carried out with a molar ratio of 3-FL to LNT of 1:2 to 1:3 and a conversion rate of 40-70%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 2-8 and a molar ratio of 3-FL to LNT of 0.13-0A can be made.

When a process of the third or the fourth aspect is carried out with a molar ratio of 3-FL to LNT of 1:3 to 1:5 and a conversion rate of 50-80%, an HMO mixture consisting essentially of 3-FL, LNT, LNFP-II and lactose, or an HMO mixture consisting essentially of 3-FL, LNT and LNFP-II, respectively, having a molar ratio of (3-FL+LNT) to LNFP-II of 3-10 and a molar ratio of 3-FL to LNT of 0.05-0.2 can be made.

When a process of the third or the fourth aspect is carried out with a molar ratio of 3-FL to LNnT of 2:1 to 1:2 and a conversion rate of 35-70%, an HMO mixture consisting essentially of 3-FL, LNnT, LNFP-III and lactose, or an HMO mixture consisting essentially of 3-FL, LNnT and LNFP-III, respectively, having a molar ratio of (3-FL+LNnT) to LNFP-III of 0.8-6.6 and a molar ratio of 3-FL to LNnT of 0.2-4.5 can be made.

When a process of the third or the fourth aspect is carried out with a molar ratio of 3-FL to LNnT of 1:1 and a conversion rate of 35-70%, an HMO mixture consisting essentially of 3-FL, LNnT, LNFP-III and lactose, or an HMO mixture consisting essentially of 3-FL, LNnT and LNFP-III, respectively, having a molar ratio of (3-FL+LNnT) to LNFP-III of 0.8-3.8 and a molar ratio of 3-FL to LNnT of 1 can be made.

When a process of the third or the fourth aspect is carried out with a molar ratio of 3-FL to LNnT of 3:1 to 1:3 and a conversion rate of 40-70%, an HMO mixture consisting essentially of 3-FL, LNnT, LNFP-III and lactose, or an HMO mixture consisting essentially of 3-FL, LNnT and LNFP-III, respectively, having a molar ratio of (3-FL+LNnT) to LNFP-III of 0.8-8 and a molar ratio of 3-FL to LNnT of 0.13-7.7 can be made.

When a process of the third or the fourth aspect is carried out with a molar ratio of 3-FL to LNnT of 2:1 to 1:2 and a conversion rate of 40-70%, an HMO mixture consisting essentially of 3-FL, LNnT, LNFP-III and lactose, or an HMO mixture consisting essentially of 3-FL, LNnT and LNFP-III, respectively, having a molar ratio of (3-FL+LNnT) to LNFP-III of 0.8-5.5 and a molar ratio of 3-FL to LNnT of 0.2-4.5 can be made.

When a process of the third or the fourth aspect is carried out with a molar ratio of 3-FL to LNnT of 1:1 and a conversion rate of 40-70%, an HMO mixture consisting essentially of 3-FL, LNnT, LNFP-III and lactose, or an HMO mixture consisting essentially of 3-FL, LNnT and LNFP-III, respectively, having a molar ratio of (3-FL+LNnT) to LNFP-III of 0.8-3 and a molar ratio of 3-FL to LNnT of 1 can be made.

When a process of the third or the fourth aspect is carried out with a molar ratio of 3-FL to LNnT of 3:1 to 1:3 and a conversion rate of 50-70%, an HMO mixture consisting essentially of 3-FL, LNnT, LNFP-III and lactose, or an HMO mixture consisting essentially of 3-FL, LNnT and LNFP-III, respectively, having a molar ratio of (3-FL+LNnT) to LNFP-III of 0.8-6 and a molar ratio of 3-FL to LNnT of 0.13-7.7 can be made.

When a process of the third or the fourth aspect is carried out with a molar ratio of 3-FL to LNnT of 2:1 to 1:2 and a conversion rate of 50-70%, an HMO mixture consisting essentially of 3-FL, LNnT, LNFP-III and lactose, or an HMO mixture consisting essentially of 3-FL, LNnT and LNFP-III, respectively, having a molar ratio of (3-FL+LNnT) to LNFP-III of 0.8-4 and a molar ratio of 3-FL to LNnT of 0.2-4.5 can be made.

When a process of the third or the fourth aspect is carried out with a molar ratio of 3-FL to LNnT of 1:1 and a conversion rate of 50-70%, an HMO mixture consisting essentially of 3-FL, LNnT, LNFP-III and lactose, or an HMO mixture consisting essentially of 3-FL, LNnT and LNFP-III, respectively, having a molar ratio of (3-FL+LNnT) to LNFP-III of 0.8-2 and a molar ratio of 3-FL to LNnT of 1 can be made.

When a process of the third or the fourth aspect is carried out with a molar ratio of 3-FL to LNnT of 3:1 to 1:3 and a conversion rate of 40-60%, an HMO mixture consisting essentially of 3-FL, LNnT, LNFP-III and lactose, or an HMO mixture consisting essentially of 3-FL, LNnT and LNFP-III, respectively, having a molar ratio of (3-FL+LNnT) to LNFP-III of 1.3-8 and a molar ratio of 3-FL to LNnT of 0.17-6 can be made.

When a process of the third or the fourth aspect is carried out with a molar ratio of 3-FL to LNnT of 2:1 to 1:2 and a conversion rate of 40-60%, an HMO mixture consisting essentially of 3-FL, LNnT, LNFP-III and lactose, or an HMO mixture consisting essentially of 3-FL, LNnT and LNFP-III, respectively, having a molar ratio of (3-FL+LNnT) to LNFP-III of 2-6.6 and a molar ratio of 3-FL to LNnT of 0.25-3.5 can be made.

When a process of the third or the fourth aspect is carried out with a molar ratio of 3-FL to LNnT of 1:1 and a conversion rate of 40-60%, an HMO mixture consisting essentially of 3-FL, LNnT, LNFP-III and lactose, or an HMO mixture consisting essentially of 3-FL, LNnT and LNFP-III, respectively, having a molar ratio of (3-FL+ LNnT) to LNFP-III of 1.3-3 and a molar ratio of 3-FL to LNnT of 1 can be made.

When a process of the third or the fourth aspect is carried out with a molar ratio of 3-FL to LNnT of 5:1 to 3:1 and a conversion rate of 50-80%, an HMO mixture consisting essentially of 3-FL, LNnT, LNFP-III and lactose, or an HMO mixture consisting essentially of 3-FL, LNnT and LNFP-III, respectively, having a molar ratio of (3-FL+ LNnT) to LNFP-III of 3-10 and a molar ratio of 3-FL to LNnT of 5-21 can be made.

When a process of the third or the fourth aspect is carried out with a molar ratio of 3-FL to LNnT of 3:1 to 2:1 and a conversion rate of 40-70%, an HMO mixture consisting essentially of 3-FL, LNnT, LNFP-III and lactose, or an HMO mixture consisting essentially of 3-FL, LNnT and LNFP-III, respectively, having a molar ratio of (3-FL+ LNnT) to LNFP-III of 2-8 and a molar ratio of 3-FL to LNnT of 2.5-7.7 can be made.

When a process of the third or the fourth aspect is carried out with a molar ratio of 3-FL to LNnT of 2:1 to 1:1 and a conversion rate of 35-55%, an HMO mixture consisting essentially of 3-FL, LNnT, LNFP-III and lactose, or an HMO mixture consisting essentially of 3-FL, LNnT and LNFP-III, respectively, having a molar ratio of (3-FL+ LNnT) to LNFP-III of 1.6-6.6 and a molar ratio of 3-FL to LNnT of 1-3.3 can be made.

When a process of the third or the fourth aspect is carried out with a molar ratio of 3-FL to LNnT of 1:1 to 1:2 and a conversion rate of 35-55%, an HMO mixture consisting essentially of 3-FL, LNnT, LNFP-III and lactose, or an HMO mixture consisting essentially of 3-FL, LNnT and LNFP-III, respectively, having a molar ratio of (3-FL+ LNnT) to LNFP-III of 1.6-6.6 and a molar ratio of 3-FL to LNnT of 0.3-1 can be made.

When a process of the third or the fourth aspect is carried out with a molar ratio of 3-FL to LNnT of 1:2 to 1:3 and a conversion rate of 40-70%, an HMO mixture consisting essentially of 3-FL, LNnT, LNFP-III and lactose, or an HMO mixture consisting essentially of 3-FL, LNnT and LNFP-III, respectively, having a molar ratio of (3-FL+ LNnT) to LNFP-III of 2-8 and a molar ratio of 3-FL to LNnT of 0.13-0.4 can be made.

When a process of the third or the fourth aspect is carried out with a molar ratio of 3-FL to LNnT of 1:3 to 1:5 and a conversion rate of 50-80%, an HMO mixture consisting essentially of 3-FL, LNnT, LNFP-III and lactose, or an HMO mixture consisting essentially of 3-FL, LNnT and LNFP-III, respectively, having a molar ratio of (3-FL+ LNnT) to LNFP-III of 3-10 and a molar ratio of 3-FL to LNnT of 0.05-0.2 can be made.

When a process of the third or the fourth aspect is carried out with a molar ratio of 3-FL to LNFP-I of 2:1 to 1:2 and a conversion rate of 35-70%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+ LNFP-I) to LNDFH-I of 0.8-6.6 and a molar ratio of 3-FL to LNFP-I of 0.2-4.5 can be made.

When a process of the third or the fourth aspect is carried out with a molar ratio of 3-FL to LNFP-I of 1:1 and a conversion rate of 35-70%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+ LNFP-I) to LNDFH-I of 0.8-3.8 and a molar ratio of 3-FL to LNFP-I of 1 can be made.

When a process of the third or the fourth aspect is carried out with a molar ratio of 3-FL to LNFP-I of 3:1 to 1:3 and a conversion rate of 40-70%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+ LNFP-I) to LNDFH-I of 0.8-8 and a molar ratio of 3-FL to LNFP-I of 0.13-7.7 can be made.

When a process of the third or the fourth aspect is carried out with a molar ratio of 3-FL to LNFP-I of 2:1 to 1:2 and a conversion rate of 40-70%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+ LNFP-I) to LNDFH-I of 0.8-5.5 and a molar ratio of 3-FL to LNFP-I of 0.2-4.5 can be made.

When a process of the third or the fourth aspect is carried out with a molar ratio of 3-FL to LNFP-I of 1:1 and a conversion rate of 40-70%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+ LNFP-I) to LNDFH-I of 0.8-3 and a molar ratio of 3-FL to LNFP-I of 1 can be made.

When a process of the third or the fourth aspect is carried out with a molar ratio of 3-FL to LNFP-I of 3:1 to 1:3 and a conversion rate of 50-70%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+ LNFP-I) to LNDFH-I of 0.8-6 and a molar ratio of 3-FL to LNFP-I of 0.13-7.7 can be made.

When a process of the third or the fourth aspect is carried out with a molar ratio of 3-FL to LNFP-I of 2:1 to 1:2 and a conversion rate of 50-70%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+ LNFP-I) to LNDFH-I of 0.8-4 and a molar ratio of 3-FL to LNFP-I of 0.2-4.5 can be made.

When a process of the third or the fourth aspect is carried out with a molar ratio of 3-FL to LNFP-I of 1:1 and a conversion rate of 50-70%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+ LNFP-I) to LNDFH-I of 0.8-2 and a molar ratio of 3-FL to LNFP-I of 1 can be made.

When a process of the third or the fourth aspect is carried out with a molar ratio of 3-FL to LNFP-I of 3:1 to 1:3 and a conversion rate of 40-60%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+ LNFP-I) to LNDFH-I of 1.3-8 and a molar ratio of 3-FL to LNFP-I of 0.17-6 can be made.

When a process of the third or the fourth aspect is carried out with a molar ratio of 3-FL to LNFP-I of 2:1 to 1:2 and a conversion rate of 40-60%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+ LNFP-I) to LNDFH-I of 2-6.6 and a molar ratio of 3-FL to LNFP-I of 0.25-3.5 can be made.

When a process of the third or the fourth aspect is carried out with a molar ratio of 3-FL to LNFP-I of 1:1 and a conversion rate of 40-60%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+LNFP-I) to LNDFH-I of 1.3-3 and a molar ratio of 3-FL to LNFP-I of 1 can be made.

When a process of the third or the fourth aspect is carried out with a molar ratio of 3-FL to LNFP-I of 5:1 to 3:1 and a conversion rate of 50-80%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+LNFP-I) to LNDFH-I of 3-10 and a molar ratio of 3-FL to LNFP-I of 5-21 can be made.

When a process of the third or the fourth aspect is carried out with a molar ratio of 3-FL to LNFP-I of 3:1 to 2:1 and a conversion rate of 40-70%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+LNFP-I) to LNDFH-I of 2-8 and a molar ratio of 3-FL to LNFP-I of 2.5-7.7 can be made.

When a process of the third or the fourth aspect is carried out with a molar ratio of 3-FL to LNFP-I of 2:1 to 1:1 and a conversion rate of 35-55%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+LNFP-I) to LNDFH-I of 1.6-6.6 and a molar ratio of 3-FL to LNFP-I of 1-3.3 can be made.

When a process of the third or the fourth aspect is carried out with a molar ratio of 3-FL to LNFP-I of 1:1 to 1:2 and a conversion rate of 35-55%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+LNFP-I) to LNDFH-I of 1.6-6.6 and a molar ratio of 3-FL to LNFP-I of 0.3-1 can be made.

When a process of the third or the fourth aspect is carried out with a molar ratio of 3-FL to LNFP-I of 1:2 to 1:3 and a conversion rate of 40-70%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+LNFP-I) to LNDFH-I of 2-8 and a molar ratio of 3-FL to LNFP-I of 0.13-0.4 can be made.

When a process of the third or the fourth aspect is carried out with a molar ratio of 3-FL to LNFP-I of 1:3 to 1:5 and a conversion rate of 50-80%, an HMO mixture consisting essentially of 3-FL, LNFP-I, LNDFH-I and lactose, or an HMO mixture consisting essentially of 3-FL, LNFP-I and LNDFH-I, respectively, having a molar ratio of (3-FL+LNFP-I) to LNDFH-I of 3-10 and a molar ratio of 3-FL to LNFP-I of 0.05-0.2 can be made.

An HMO mixture consisting essentially of 3-FL, 2'-FL, DFL and lactose or consisting essentially of 3-FL, 2'-FL and DFL can be obtained by carrying out a process of the third or the fourth aspect, respectively, with 3-FL and 2'-FL in a molar ratio of preferably 1:5 to 5:1, more preferably 1:3 to 3:1, even more preferably 1:2 to 2:1, yet even preferably 1:1, and with an α1-3/4 transfucosidase having a conversion rate of at least 35%, up to about 70%, preferably at least 40%, more preferably at least 50%.

When a process of the third or the fourth aspect is carried out with a molar ratio of 3-FL to 2'-FL of 2:1 to 1:2 and a conversion rate of 35-70%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 0.8-6.6 and a molar ratio of 3-FL to 2'-FL of 0.2-4.5 can be made.

When a process of the third or the fourth aspect is carried out with a molar ratio of 3-FL to 2'-FL of 1:1 and a conversion rate of 35-70%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 0.8-3.8 and a molar ratio of 3-FL to 2'-FL of 1 can be made.

When a process of the third or the fourth aspect is carried out with a molar ratio of 3-FL to 2'-FL of 3:1 to 1:3 and a conversion rate of 40-70%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 0.8-8 and a molar ratio of 3-FL to 2'-FL of 0.13-7.7 can be made.

When a process of the third or the fourth aspect is carried out with a molar ratio of 3-FL to 2'-FL of 2:1 to 1:2 and a conversion rate of 40-70%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 0.8-5.5 and a molar ratio of 3-FL to 2'-FL of 0.2-4.5 can be made.

When a process of the third or the fourth aspect is carried out with a molar ratio of 3-FL to 2'-FL of 1:1 and a conversion rate of 40-70%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 0.8-3 and a molar ratio of 3-FL to 2'-FL of 1 can be made.

When a process of the third or the fourth aspect is carried out with a molar ratio of 3-FL to 2'-FL of 3:1 to 1:3 and a conversion rate of 50-70%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 0.8-6 and a molar ratio of 3-FL to 2'-FL of 0.13-7.7 can be made.

When a process of the third or the fourth aspect is carried out with a molar ratio of 3-FL to 2'-FL of 2:1 to 1:2 and a conversion rate of 50-70%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 0.8-4 and a molar ratio of 3-FL to 2'-FL of 0.2-4.5 can be made.

When a process of the third or the fourth aspect is carried out with a molar ratio of 3-FL to 2'-FL of 1:1 and a conversion rate of 50-70%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 0.8-2 and a molar ratio of 3-FL to 2'-FL of 1 can be made.

When a process of the third or the fourth aspect is carried out with a molar ratio of 3-FL to 2'-FL of 3:1 to 1:3 and a conversion rate of 40-60%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 1.3-8 and a molar ratio of 3-FL to 2'-FL of 0.17-6 can be made.

When a process of the third or the fourth aspect is carried out with a molar ratio of 3-FL to 2'-FL of 2:1 to 1:2 and a conversion rate of 40-60%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 2-6.6 and a molar ratio of 3-FL to 2'-FL of 0.25-3.5 can be made.

When a process of the third or the fourth aspect is carried out with a molar ratio of 3-FL to 2'-FL of 1:1 and a conversion rate of 40-60%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 1.3-3 and a molar ratio of 3-FL to 2'-FL of 1 can be made.

When a process of the third or the fourth aspect is carried out with a molar ratio of 3-FL to 2'-FL of 5:1 to 3:1 and a conversion rate of 50-80%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 3-10 and a molar ratio of 3-FL to 2'-FL of 5-21 can be made.

When a process of the third or the fourth aspect is carried out with a molar ratio of 3-FL to 2'-FL of 3:1 to 2:1 and a conversion rate of 40-70%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 2-8 and a molar ratio of 3-FL to 2'-FL of 2.5-7.7 can be made.

When a process of the third or the fourth aspect is carried out with a molar ratio of 3-FL to 2'-FL of 2:1 to 1:1 and a conversion rate of 35-55%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 1.6-6.6 and a molar ratio of 3-FL to 2'-FL of 1-3.3 can be made.

When a process of the third or the fourth aspect is carried out with a molar ratio of 3-FL to 2'-FL of 1:1 to 1:2 and a conversion rate of 35-55%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 1.6-6.6 and a molar ratio of 3-FL to 2'-FL of 0.3-1 can be made.

When a process of the third or the fourth aspect is carried out with a molar ratio of 3-FL to 2'-FL of 1:2 to 1:3 and a conversion rate of 40-70%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 2-8 and a molar ratio of 3-FL to 2'-FL of 0.13-0.4 can be made.

When a process of the third or the fourth aspect is carried out with a molar ratio of 3-FL to 2'-FL of 1:3 to 1:5 and a conversion rate of 50-80%, an HMO mixture consisting essentially of 3-FL, 2'-FL, DFL and lactose, or an HMO mixture consisting essentially of 3-FL, 2'-FL and DFL, respectively, having a molar ratio of (3-FL+2'-FL) to DFL of 3-10 and a molar ratio of 3-FL to 2'-FL of 0.05-0.2 can be made.

The α1-3/4 transfucosidase suitable for carrying out the third and the fourth aspect of the invention In the following paragraphs, the expression "may carry" is equivalent with the expression "optionally carries", and the expression "can be substituted" is equivalent with the expression "is optionally substituted".

In accordance with this invention, the term "α1-3/4 transfucosidase" preferably means any wild type or engineered fucosidase that is able to transfer a fucose residue to the 3-position of the glucose in an acceptor of formula 2, to the 3-position of the N-acetyl-glucosamine in a, preferably terminal, N-acetyl-lactosaminyl group in an acceptor of formula 1, 1a or 1b, or to the 4-position of the N-acetyl-glucosamine in a, preferably terminal, lacto-N-biosyl group, in an acceptor of formula 1, 1a or 1b, where the compounds of formulae 1 and 2 are as follows:

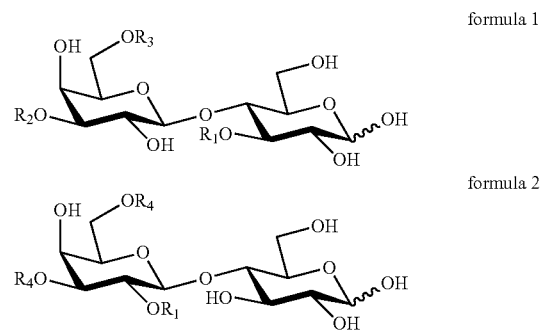

wherein $R_1$ is fucosyl or H, $R_2$ is selected from N-acetyl-lactosaminyl and lacto-N-biosyl groups, wherein the N-acetyl lactosaminyl group may carry a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue, $R_3$ is H or N-acetyl-lactosaminyl group optionally substituted with a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue, and each $R_4$ independently is sialyl or H, with the proviso that at least one of $R_1$ or $R_4$ is not H;
and the compounds of formulae 1a and 1b are as follows:

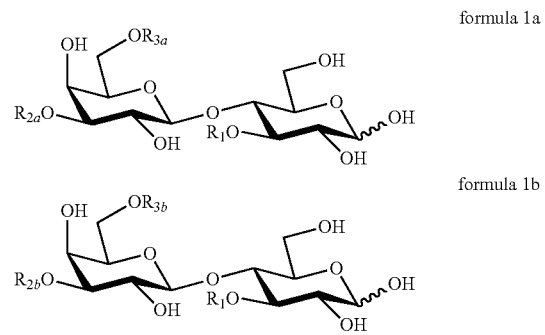

wherein $R_1$ is as defined above, $R_{2a}$ is an N-acetyl-lactosaminyl group optionally substituted with a glycosyl residue comprising one N-acetyl-lactosaminyl and/or one lacto-N-biosyl group; any N-acetyl-lactosaminyl and lacto-N-biosyl group can be substituted with one or more sialyl and/or fucosyl residue, but preferably void of a sialyl and/or fucosyl residue, $R_{3a}$ is H or an N-acetyl-lactosaminyl group optionally substituted with a lacto-N-biosyl group; any N-acetyllactosaminyl and lacto-N-biosyl group can be substituted with one or more sialyl and/or fucosyl residue, but preferably void of a sialyl and/or fucosyl residue, $R_{2b}$ is a lacto-N-biosyl group optionally substituted with sialyl and/or fucosyl residue, but preferably void of a sialyl and/or fucosyl residue, and $R_{3b}$ is H or an N-acetyl-lactosaminyl group optionally substituted with one or two N-acetyl-lactosaminyl and/or one lacto-N-biosyl group; any N-acetyl-lactosaminyl and lacto-N-biosyl group can be substituted with one or more sialyl and/or fucosyl residue, but preferably without a sialyl and/or fucosyl residue.

Preferably, the compounds of formulae 1a and 1b have one or more of the following linkages and modifications:

the N-acetyl-lactosaminyl group in the glycosyl residue of $R_{2a}$ in formula 1a is attached to the another N-acetyl-lactosaminyl group by a 1-3 interglycosidic linkage, the lacto-N-biosyl group in the glycosyl residue of $R_{2a}$ in formula 1a is attached to the N-acetyl-lactosaminyl group by a 1-3 interglycosidic linkage, the lacto-N-biosyl group in the glycosyl residue of $R_{3a}$ in formula 1a is attached to the N-acetyl-lactosaminyl group by a 1-3 interglycosidic linkage, the N-acetyl-lactosaminyl group in the glycosyl residue of $R_{3b}$ in formula 1 b is attached to another N-acetyl-lactosaminyl group by a 1-3 or 1-6 interglycosidic linkage, and the lacto-N-biosyl group in the glycosyl residue of $R_{3b}$ in formula 1b is attached to the N-acetyl-lactosaminyl group by a 1-3 interglycosidic linkage.

The α1-3/4 transfucosidase is preferably selected from α-L-fucosidases as classified according to EC 3.2.1.111, having transfucosidase activity, such as the α1-3/4 fucosidase from *Bifidobacterium longum* subsp. *infantis* ATCC 15697 as set forth in U.S. Pat. No. 8,361,756 as protein of SEQ ID No. 18 (SEQ ID No. 1 of the present application) and other fucosidases which have at least 60%, preferably at least 70%, more preferably at least 80%, particularly at least 90%, identity with amino acid positions 56 to 345 of the α1-3/4 fucosidase from *Bifidobacterium longum* subsp. *infantis* ATCC 15697. Examples of such other fucosidases are listed below in Table 1.

TABLE 1

| Description | Accession No. |
|---|---|
| α-L-fucosidase [*Bifidobacterium longum* subsp. *infantis* EK3] | KEY30716.1 |
| α-L-fucosidase [*Bifidobacterium longum*] | WP_013140205.1 |
| putative α1-3/4 fucosidase [*Bifidobacterium kashiwanohense* JCM 15439] | KFI63931.1 |
| putative α1-3/4 fucosidase [*Bifidobacterium scardovii*] | KFI94501.1 |
| α-L-fucosidase [*Gardnerella vaginalis*] | WP_004574432.1 |
| α-L-fucosidase [*Gardnerella vaginalis*] | WP_019261748.1 |
| hypothetical protein [*Gardnerella vaginalis*] | WP_020759655.1 |
| α-L-fucosidase [*Gardnerella vaginalis*] | WP_009993891.1 |
| α-L-fucosidase [*Gardnerella vaginalis*] | WP_004573610.1 |
| α-L-fucosidase [*Gardnerella vaginalis*] | WP_004120276.1 |
| α-L-fucosidase [*Gardnerella vaginalis*] | WP_004114072.1 |
| α-L-fucosidase [*Gardnerella vaginalis*] | WP_004137675.1 |
| α-L-fucosidase [*Gardnerella vaginalis*] | WP_014554869.1 |
| α-L-fucosidase [*Bifidobacterium bifidum* CAG: 234] | WP_022173522.1 |
| α-L-fucosidase [*Actinomyces* sp. ICM47] | WP_009647833.1 |
| hypothetical protein [*Streptomyces ipomoeae*] | WP_009295550.1 |
| α-L-fucosidase [*Actinomyces* sp. oral taxon 180] | WP_009211856.1 |

TABLE 1-continued

| Description | Accession No. |
|---|---|
| hypothetical protein [*Actinomyces* sp. oral taxon 172] | WP_021611755.1 |
| α-L-fucosidase [*Bifidobacterium* sp. 7101] | WP_029678277.1 |
| hypothetical protein [*Actinomyces* sp. HPA0247] | WP_016461038.1 |
| α-L-fucosidase [*Actinomyces* sp. ICM54] | EWC96238.1 |
| α-L-fucosidase [*Actinomyces odontolyticus*] | WP_003795385.1 |
| α-L-fucosidase [*Atopobium* sp. ICM58] | WP_009055210.1 |
| α-L-fucosidase [*Paenibacillus* sp. J14] | WP_028538247.1 |
| α-L-fucosidase [*Actinomyces odontolyticus*] | WP_003792781.1 |
| α1-3/4 fucosidase [*Propionibacterium acidipropionici*] | WP_015071771.1 |
| α-L-fucosidase [*Propionibacterium acidipropionici*] | WP_028700846.1 |
| hypothetical protein [*Paenibacillus barengoltzii*] | WP_016312877.1 |
| α-L-fucosidase [*Actinomyces* sp. ICM39] | WP_007588699.1 |
| α-L-fucosidase [*Propionibacterium jensenii*] | WP_028703334.1 |
| α-L-fucosidase [*Lactobacillus shenzhenensis*] | WP_022529554.1 |
| hypothetical protein [*Paenibacillus* sp. HW567] | WP_019912449.1 |
| putative α-1 3/4-fucosidase [*Clostridium hathewayi* CAG: 224] | WP_022032399.1 |
| α-fucosidase [*Clostridium hathewayi*] | WP_006775425.1 |
| α-L-fucosidase [*Janibacter* sp. HTCC2649] | WP_009776262.1 |
| α-fucosidase [*Clostridium phytofermentans*] | WP_012201036.1 |
| α-L-fucosidase [*Enterococcus gallinarum*] | WP_029486307.1 |
| uncharacterized protein [*Blautia* sp. CAG: 237] | WP_022215646.1 |
| MULTISPECIES: α-L-fucosidase [*Enterococcus*] | WP_005470131.1 |
| α-L-fucosidase [*Enterococcus gallinarum* EG2] | EEV33648.1 |
| α-L-fucosidase [*Ruminococcus* sp. CAG: 60] | CCY33010.1 |
| α-L-fucosidase [*Ruminococcus* sp. CAG: 9] | WP_022380664.1 |
| α-fucosidase [*Blautia wexlerae*] | WP_025580031.1 |
| α-fucosidase [*Ruminococcus* sp. 5_1_39BFAA] | WP_008706707.1 |
| α-fucosidase [*Paenibacillus* sp. HGF5] | WP_009593620.1 |
| α-L-fucosidase [*Paenibacillus* sp. FSL H8-457] | ETT68114.1 |
| hypothetical protein [*Clostridium hathewayi*] | WP_002604401.1 |
| hypothetical protein [*Paenibacillus* sp. PAMC 26794] | WP_017691196.1 |
| α-L-fucosidase [*Paenibacillus* sp. FSL R5-192] | ETT29638.1 |
| α-fucosidase [*Paenibacillus* sp. Y412MC10] | WP_015736742.1 |
| α-L-fucosidase [*Paenibacillus alvei*] | WP_021262981.1 |
| α-fucosidase [*Paenibacillus* sp. UNC217MF] | WP_028532504.1 |
| α-fucosidase [*Paenibacillus alvei*] | WP_005546194.1 |
| α-L-fucosidase [*Paenibacillus alvei*] | WP_021254840.1 |
| hypothetical protein [*Paenibacillus terrigena*] | WP_018756045.1 |
| α-fucosidase [*Ruminococcus obeum*] | WP_005422251.1 |
| α-L-fucosidase [*Paenibacillus* sp. FSL H7-689] | ETT43086.1 |
| α-fucosidase [*Paenibacillus lactis*] | WP_007127626.1 |
| α-fucosidase [*Bacillus* sp. J13] | WP_028406965.1 |
| hypothetical protein [*Paenibacillus daejeonensis*] | WP_020617104.1 |
| hypothetical protein [*Clostridium* sp. KLE 1755] | WP_021638714.1 |
| α-fucosidase [*Clostridium* sp. ASBs410] | WP_025233568.1 |
| α-fucosidase [*Paenibacillus vortex*] | WP_006211772.1 |
| α-L-fucosidase [*Paenibacillus* sp. FSL R5-808] | ETT35249.1 |
| α-fucosidase [*Clostridium celerecrescens*] | KEZ90324.1 |
| α-L-fucosidase [*Firmicutes bacterium* CAG: 94] | WP_022336739.1 |
| α-fucosidase [*Clostridiales bacterium* VE202-27] | WP_025488431.1 |
| α-fucosidase [*Paenibacillus pasadenensis*] | WP_028597616.1 |
| MULTISPECIES: α-fucosidase [*Paenibacillus*] | WP_024629466.1 |
| α-fucosidase [*Paenibacillus* sp. UNC451MF] | WP_028551519.1 |
| α-fucosidase [*Paenibacillus* sp. PAMC 26794] | WP_026081066.1 |
| α-fucosidase [*Paenibacillus* sp. JDR-2] | WP_015843379.1 |
| MULTISPECIES: α-fucosidase [*Clostridiales*] | WP_009250084.1 |
| α-fucosidase [*Clostridium saccharolyticum*] | WP_013273060.1 |

It is important that the transfucosidase activity of the α1-3/4 transfucosidase is greater than its hydrolytic activity. In the course of the 3-FL+component B ⇌ component C+Lac or DFL+component E ⇌ component F+2'-FL reaction the hydrolysis of the component C or component F can become significant at a certain time point, due to the increasing concentration of the component C or component F, which are then degraded into component B or component E, respectively, and fucose. In order to prepare the HMO mixtures of the invention, the reaction should be stopped before there is significant product hydrolysis. This time point can be easily determined by well-known enzyme kinetic measurements.

Especially preferred α1-3/4 transfucosidases for making the HMO mixtures of this invention are the α1-3/4 transfucosidases that lack hydrolytic activity, or at least have significantly reduced hydrolytic activity. Such enzymes can be made by altering the amino acid sequence of a mainly wild type, α1-3/4 fucosidase at one or more amino acid positions, so that the mutated amino acid sequence results in improved transfucosidase activity and/or reduced hydrolytic activity. In accordance with this invention, the α1-3/4 transfucosidase preferably:

i) has been mutated at least at one or more of the following amino acid positions of SEQ ID No. 18 of U.S. Pat. No. 8,361,756: 134, 135, 168, 170, 174, 216, 221, 236, 237, 244, 245, 282 and 413, preferably at least at one or more of the following amino acid positions: 134, 135, 174, 216, 221, 282 and 413; and thereby ii) provides a conversion rate of at least 10% up to 70%, preferably at least 20%, more preferably at least 35%, even more preferably 40-50%, for the reaction of
the 3-FL donor with the LNT acceptor, or
the 3-FL donor with the LNnT acceptor, or
the 3-FL donor with the LNFP-I acceptor, or
the 3-FL donor with the 2'-FL acceptor, or
the DFL donor with the LNT acceptor, or
the DFL donor with the LNnT acceptor, or
the DFL donor with the LNFP-I acceptor.

The Fifth Aspect of the Invention

The fifth aspect of this invention is an anti-infective composition for treating bacterial infections. The composition comprises, preferably consists essentially of:
DFL,
a component E which is LNT, LNnT or LNFP-1,
a component F, which is:
LNFP-II when component E is LNT, or
LNFP-III when component E is LNnT, or
LNDFH-I when component E is LNFP-I, and
2'-FL,
or comprises, preferably consists essentially of:
3-FL,
a component B which is LNT, LNnT, LNFP-I or 2'-FL, and
a fucosylated component C, which is:
LNFP-II when component B is LNT, or
LNFP-III when component B is LNnT, or
LNDFH-I when component B is LNFP-I, or
DFL when component B is 2'-FL;
or the composition consists essentially of
3-FL,
a component B which is LNT, LNnT, LNFP-I or 2'-FL,
a fucosylated component C, which is
LNFP-II when component B is LNT, or
LNFP-III when component B is LNnT, or
LNDFH-I when component B is LNFP-I, or
DFL when component B is 2'-FL, and
lactose;
preferably the anti-infective composition consists essentially of
3-FL,
a component B which is LNT, LNnT, LNFP-I or 2'-FL, and
a component C, which is
LNFP-II when component B is LNT, or
LNFP-III when component B is LNnT, or
LNDFH-I when component B is LNFP-I, or
DFL when component B is 2'-FL,
or the anti-infective composition consists essentially of DFL,
a component E which is LNT, LNnT or LNFP-I,
a component F, which is
LNFP-II when component E is LNT, or
LNFP-III when component E is LNnT, or
LNDFH-I when component E is LNFP-I, and
2'-FL.

The especially preferred anti-infective composition is selected from the group consisting of:
a mixture of HMOs consisting essentially of 3-FL, LNT and LNFP-II or of 3-FL, LNT, LNFP-II and lactose, preferably in which:
the molar ratio of (3-FL+LNT) relative to LNFP-II is 0.8-9.5, and
the molar ratio of lactose relative to LNFP-II is about 1, provided that one of the molar ratios 3-FL to LNFP-II and LNT to LNFP-II is not more than 2, particularly a mixture of HMOs consisting essentially of 3-FL, LNT and LNFP-II; or
a mixture of HMOs consisting essentially of 3-FL, LNnT and LNFP-III or of 3-FL, LNnT, LNFP-III and lactose, preferably in which:
the molar ratio of (3-FL+LNnT) relative to LNFP-III is 0.8-9.5 and
the molar ratio of lactose relative to LNFP-III is about 1, provided that one of the molar ratios 3-FL to LNFP-III and LNnT to LNFP-III is not more than 2, particularly a mixture of HMOs consisting essentially of 3-FL, LNnT and LNFP-III; or
a mixture of HMOs consisting essentially of 3-FL, LNFP-I and LNDFH-I or of 3-FL, LNFP-I, LNDFH-I and lactose, preferably in which:
the molar ratio of (3-FL+LNFP-I) relative to LNDFH-I is 0.8-9.5 and
the molar ratio of lactose relative to LNDFH-I is about 1, particularly a mixture of HMOs consisting essentially of 3-FL, LNFP-I and LNDFH-I; or
a mixture of HMOs consisting essentially of 3-FL, 2'-FL and DFL or of 3-FL, 2'-FL, DFL and lactose, preferably in which:
the molar ratio of (3-FL+2'-FL) relative to DFL is 0.8-9.5 and
the molar ratio of lactose relative to DFL is about 1; or
a mixture of HMOs consisting essentially of 3-FL, 2'-FL and DFL, preferably in which:
the molar ratio of DFL relative to (3-FL+2'-FL) is at least 1:10, preferably at least 1:7, more preferably at least 1:5, especially 1:3; and/or
the molar ratio of 3-FL relative to 2'-FL is 0.05-21, preferably 0.13-7.7, more preferably about 1; or
a mixture of HMOs comprising 2'-FL, DFL, LNT and LNFP-II, preferably a mixture of HMOs consisting essentially of 2'-FL, DFL, LNT and LNFP-II; or
a mixture of HMOs comprising 2'-FL, DFL, LNnT and LNFP-III-II, preferably a mixture of HMOs consisting essentially of 2'-FL, DFL, LNnT and LNFP-III; or
a mixture of HMOs comprising 2'-FL, DFL, LNFP-I and LNDFH-I, preferably a mixture of HMOs consisting essentially of 2'-FL, DFL, LNFP-I and LNDFH-I.

The anti-infective composition of this invention can be a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients.

The pharmaceutical composition can also contain other materials that do not produce an adverse, allergic or otherwise unwanted reaction when administered to a patient. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents. If desired, tablet dosages of the anti-infective compositions can be coated by standard aqueous or non-aqueous techniques.

The anti-infective compositions of this invention can be administered orally, e.g. as a tablet, capsule, or pellet containing a predetermined amount of the first mixture, or as a powder or granules containing a predetermined concentration of the first mixture or a gel, paste, solution, suspension, emulsion, syrup, bolus, electuary, or slurry, in an aqueous or non-aqueous liquid, containing a predetermined concentration of the first mixture. Orally administered compositions can include binders, lubricants, inert diluents, flavouring agents, and humectants. Orally administered compositions such as tablets can optionally be coated and can be formulated so as to provide sustained, delayed or controlled release of the first mixture therein.

The anti-infective compositions of this invention can also be administered by rectal suppository, aerosol tube, nasogastric tube or direct infusion into the GI tract or stomach.

Anti-infective pharmaceutical compositions of this invention can also include therapeutic agents such as antiviral agents, antibiotics, probiotics, analgesics, and anti-inflammatory agents. The proper dosage of these compositions for a patient can be determined in a conventional manner, based upon factors such as the patients immune status, body weight and age. In some cases, the dosage will be at a concentration similar to that found for the HMOs of the composition in human breast milk. The required amount would generally be in the range from about 200 mg to about 20 g per day, in certain embodiments from about 300 mg to about 15 g per day, from about 400 mg to about 10 g per day, in certain embodiments from about 500 mg to about 10 g per day, in certain embodiments from about 1 g to about 10 g per day. Appropriate dose regimes can be determined by methods known to those skilled in the art.

The anti-infective compositions of this invention can also be added to nutritional compositions. For example, they can be added to an infant formula, a nutritional composition, a rehydration solution, or a dietary maintenance or supplement for elderly individuals or immunocompromised individuals. Macronutrients such as edible fats, carbohydrates and proteins can also be included in such anti-infective compositions. Edible fats include, for example, coconut oil, soy oil and monoglycerides and diglycerides. Carbohydrates include, for example, glucose, edible lactose and hydrolysed cornstarch. Proteins include, for example, soy protein, whey, and skim milk. Vitamins and minerals (e. g. calcium, phosphorus, potassium, sodium, chloride, magnesium, manganese, iron, copper, zinc, selenium, iodine, and Vitamins A, E, D, C, and B complex) can also be included in such anti-infective compositions.

The Sixth Aspect of the Invention

The sixth aspect of the invention is a method of modulating the microbiome of a human to increase *Bifidobacterium* abundance and *Barnesiella* abundance. Preferably, the method reduces *Firmicutes* abundance, especially *Clostridia*. The method comprises administering to the human:

i) a composition comprising, preferably consisting essentially of,
   3-FL,
   a component B which is LNT, LNnT, LNFP-I or 2'-FL, and
   a component C, which is
      LNFP-II when component B is LNT, or
      LNFP-III when component B is LNnT, or
      LNDFH-I when component B is LNFP-I, or
      DFL when component B is 2'-FL;
or
ii) a composition consisting essentially of
   3-FL,
   a component B which is LNT, LNnT, LNFP-I or 2'-FL, and
   a component C, which is
      LNFP-II when component B is LNT, or
      LNFP-III when component B is LNnT, or
      LNDFH-I when component B is LNFP-I, or
      DFL when component B is 2'-FL; and
   lactose;
or
iii) a composition comprising, preferably consisting essentially of,
   DFL,
   a component E which is LNT, LNnT or LNFP-I,
   a component F, which is
      LNFP-II when component E is LNT, or
      LNFP-III when component E is LNnT, or
      LNDFH-I when component E is LNFP-I, and
   2'-FL,
preferably a composition consisting essentially of
   3-FL,
   a component B which is LNT, LNnT, LNFP-I or 2'-FL, and
   a component C, which is
      LNFP-II when component B is LNT, or
      LNFP-III when component B is LNnT, or
      LNDFH-I when component B is LNFP-I, or
      DFL when component B is 2'-FL,
or a composition consisting essentially of
   DFL,
   a component E which is LNT, LNnT or LNFP-I,
   a component F, which is
      LNFP-II when component E is LNT, or
      LNFP-III when component E is LNnT, or
      LNDFH-I when component E is LNFP-I, and
   2'-FL.

Especially preferred methods for modulating the microbiome of a human involve administering to the human:
   3-FL, LNT and LNFP-II, preferably a mixture of HMOs consisting essentially of 3-FL, LNT and LNFP-II or of 3-FL, LNT, LNFP-II and lactose, more preferably in which:
      the molar ratio of (3-FL+LNT) relative to LNFP-II is 0.8-9.5, and
      the molar ratio of lactose relative to LNFP-II is about 1, provided that one of the molar ratios 3-FL to LNFP-II and LNT to LNFP-II is not more than 2, particularly a mixture of HMOs consisting essentially of 3-FL, LNT and LNFP-II; or
   3-FL, LNnT and LNFP-III, preferably a mixture of HMOs consisting essentially of 3-FL, LNnT and LNFP-III or of 3-FL, LNnT, LNFP-III and lactose, more preferably in which:
      the molar ratio of (3-FL+LNnT) relative to LNFP-III is 0.8-9.5 and the molar ratio of lactose relative to LNFP-III is about 1, provided that one of the molar ratios 3-FL to LNFP-III and LNnT to LNFP-III is not more than 2, particularly a mixture of HMOs consisting essentially of 3-FL, LNnT and LNFP-III; or 3-FL, LNFP-I and LNDFH-I, preferably a mixture of HMOs consisting essentially of 3-FL, LNFP-I and LNDFH-I or of 3-FL, LNFP-I, LNDFH-I and lactose, more preferably in which:
the molar ratio of (3-FL+LNFP-I) relative to LNDFH-I is 0.8-9.5 and
the molar ratio of lactose relative to LNDFH-I is about 1, particularly a mixture of HMOs consisting essentially of 3-FL, LNFP-I and LNDFH-I; or 3-FL, 2'-FL and DFL, preferably a mixture of HMOs consisting essentially of 3-FL, 2'-FL and DFL or of 3-FL, 2'-FL, DFL and lactose, more preferably in which:
the molar ratio of (3-FL+2'-FL) relative to DFL is 0.8-9.5 and
the molar ratio of lactose relative to DFL is about 1, particularly a mixture of HMOs consisting essentially of 3-FL, 2'-FL and DFL; or 2'-FL, DFL, LNT and LNFP-II, preferably a mixture of HMOs comprising 2'-FL, DFL, LNT and LNFP-II, more preferably a mixture of HMOs consisting essentially of 2'-FL, DFL, LNT and LNFP-II; or 2'-FL, DFL, LNnT and LNFP-III, preferably a mixture of HMOs comprising 2'-FL, DFL, LNnT and LNFP-III-II, more preferably a mixture of HMOs consisting essentially of 2'-FL, DFL, LNnT and LNFP-III; or 2'-FL, DFL, LNFP-I and LNDFH-I, preferably a mixture of HMOs comprising 2'-FL, DFL, LNFP-I and LNDFH-I, more preferably a mixture of HMOs consisting essentially of 2'-FL, DFL, LNFP-I and LNDFH-I.

The Seventh Aspect of the Invention

The seven aspect of the invention is a method of preventing or treating bacterial infections in a human, especially antibiotic resistant bacterial infections. The method comprises administering to the human, i) a composition comprising, preferably consisting essentially of,
3-FL,
a component B which is LNT, LNnT, LNFP-I or 2'-FL, and
a fucosylated component C, which is
LNFP-II when component B is LNT, or
LNFP-III when component B is LNnT, or
LNDFH-I when component B is LNFP-I, or
DFL when component B is 2'-FL;
or
ii) a composition consisting essentially of
3-FL,
a component B which is LNT, LNnT, LNFP-I or 2'-FL, and
a component C, which is
LNFP-II when component B is LNT, or
LNFP-III when component B is LNnT, or
LNDFH-I when component B is LNFP-I, or
DFL when component B is 2'-FL; and
lactose;
or
iii) a composition comprising, preferably consisting essentially of,
DFL,
a component E which is LNT, LNnT or LNFP-I,
a component F, which is
LNFP-II when component E is LNT, or
LNFP-III when component E is LNnT, or
LNDFH-I when component E is LNFP-I, and
2'-FL,
preferably a composition consisting essentially of
3-FL,
a component B which is LNT, LNnT, LNFP-I or 2'-FL, and
a component C, which is
LNFP-II when component B is LNT, or
LNFP-III when component B is LNnT, or
LNDFH-I when component B is LNFP-I, or
DFL when component B is 2'-FL,
or a composition consisting essentially of
DFL,
a component E which is LNT, LNnT or LNFP-I,
a component F, which is
LNFP-II when component E is LNT, or
LNFP-III when component E is LNnT, or
LNDFH-I when component E is LNFP-I, and
2'-FL.

Especially preferred methods for preventing or treating bacterial infections in human comprises administering to the human:

3-FL, LNT and LNFP-II, preferably a mixture of HMOs consisting essentially of 3-FL, LNT and LNFP-II or of 3-FL, LNT, LNFP-II and lactose, more preferably in which:
the molar ratio of (3-FL+LNT) relative to LNFP-II is 0.8-9.5, and
the molar ratio of lactose relative to LNFP-II is about 1,
provided that one of the molar ratios 3-FL to LNFP-II and LNT to LNFP-II is not more than 2, particularly a mixture of HMOs consisting essentially of 3-FL, LNT and LNFP-II; or 3-FL, LNnT and LNFP-III, preferably a mixture of HMOs consisting essentially of 3-FL, LNnT and LNFP-III or of 3-FL, LNnT, LNFP-III and lactose, more preferably in which:
the molar ratio of (3-FL+LNnT) relative to LNFP-III is 0.8-9.5 and
the molar ratio of lactose relative to LNFP-III is about 1,
provided that one of the molar ratios 3-FL to LNFP-III and LNnT to LNFP-III is not more than 2, particularly a mixture of HMOs consisting essentially of 3-FL, LNnT and LNFP-III; or 3-FL, LNFP-I and LNDFH-I, preferably a mixture of HMOs consisting essentially of 3-FL, LNFP-I and LNDFH-I or of 3-FL, LNFP-I, LNDFH-I and lactose, more preferably in which:
the molar ratio of (3-FL+LNFP-I) relative to LNDFH-I is 0.8-9.5 and
the molar ratio of lactose relative to LNDFH-I is about 1,
particularly a mixture of HMOs consisting essentially of 3-FL, LNFP-I and LNDFH-I; or 3-FL, 2'-FL and DFL, preferably a mixture of HMOs consisting essentially of 3-FL, 2'-FL and DFL or of 3-FL, 2'-FL, DFL and lactose, more preferably in which:
the molar ratio of (3-FL+2'-FL) relative to DFL is 0.8-9.5 and
the molar ratio of lactose relative to DFL is about 1, particularly a mixture of HMOs consisting essentially of 3-FL, 2'-FL and DFL; or 2'-FL, DFL, LNT and LNFP-II, preferably a mixture of HMOs comprising 2'-FL, DFL, LNT and LNFP-II, more preferably a mixture of HMOs consisting essentially of 2'-FL, DFL, LNT and LNFP-II; or 2'-FL, DFL, LNnT and LNFP-III, preferably a mixture of HMOs comprising 2'-FL, DFL, LNnT and LNFP-III-II, more preferably a mixture of HMOs consisting essentially of 2'-FL, DFL, LNnT and LNFP-III; or 2'-FL, DFL, LNFP-I and LNDFH-I, preferably a mixture of HMOs comprising 2'-FL, DFL, LNFP-I and LNDFH-I, more preferably a mixture of HMOs consisting essentially of 2'-FL, DFL, LNFP-I and LNDFH-I.

Whilst the invention has been described with reference to preferred embodiments, it will be appreciated that various modifications are possible within the scope of the invention.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

EXAMPLES

In the examples below, mutants of *Bifidobacterium longum* subsp. *infantis* ATCC 15697 were used for making mixtures of this invention; the positions of mutations are with reference to SEQ ID No. 1 of this application, which is identical with SEQ ID No. 18 of U.S. Pat. No. 8,361,756.

Example 1

3-FL+LNT ⇌ LNFP-II+Lac

The test was run in sodium phosphate buffer (50 mM, pH=6.5, 37° C., 200 μl), [3-FL]=200 mM, [LNT]=200 mM, enzyme extract=0.5 mg/ml. HPLC conditions: TSK Gel amide 80 (Tosoh, 3 μm, 150×4.6 mm) was used with a flow of 1 ml/min using 56% acetonitrile and 44% water. The elution of substrates and products was detected by CAD and/or UV detection at 195 nm.

The table below shows the composition of mixtures obtained. Lactose is equimolar to LNFP-II.

| mutant | conversion, time | molar ratio | | |
|---|---|---|---|---|
| | | 3-FL | LNT | LNFP-II |
| N216D | 43.9%, 15 min | 1.28 | 1.28 | 1 |
| V221A | 35.6%, 15 min | 1.81 | 1.81 | 1 |
| V282K | 39.7%, 4 h | 1.52 | 1.52 | 1 |
| P134A | 36.4%, 4 h | 1.75 | 1.75 | 1 |
| W135F | 44.5%, 15 min | 1.25 | 1.25 | 1 |
| W135A | 39.5%, 2 h | 1.53 | 1.53 | 1 |
| W135A | 46.1%, 6.5 h | 1.17 | 1.17 | 1 |
| W135E | 39.4%, 15 min | 1.54 | 1.54 | 1 |
| W135E | 43.2%, 30 min | 1.31 | 1.31 | 1 |
| W135E | 45.2%, 1 h | 1.21 | 1.21 | 1 |
| A174S | 45.1%, 15 min | 1.22 | 1.22 | 1 |
| Q244K | 37.6%, 15 min | 1.66 | 1.66 | 1 |
| Q244K | 45.1%, 1 h | 1.22 | 1.22 | 1 |
| Q244K | 50.5%, 6.5 h | 0.98 | 0.98 | 1 |
| S168E-A174H-E413R | 41.1%, 2 h | 1.43 | 1.43 | 1 |
| S168E-A174H-E413R | 48.7%, 23 h | 1.05 | 1.05 | 1 |
| S168E-A174H-V282E | 37.8%, 1 h | 1.65 | 1.65 | 1 |
| S168E-A174H-V282E | 48.5%, 6 h | 1.06 | 1.06 | 1 |
| S168E-A174H-V221A-V282H | 48.5%, 6 h | 1.06 | 1.06 | 1 |
| W135E-A174F-V221A | 47.4%, 6 h | 1.11 | 1.11 | 1 |

Example 2

The same test was carried out, using the W135F-A174N-N274A-E413 mutant, as in Example 1 with the difference that the 3-FL:LNT ratio varied from 3:1 to 1:3, and the enzyme extract was 0.05 mg/ml). The table below shows the composition of mixtures obtained. Lactose is equimolar to LNFP-II. No fucose was detected.

| 3-FL/LNT ratio | conversion, time | molar ratio | | |
|---|---|---|---|---|
| | | 3-FL | LNT | LNFP-II |
| 3:1 | 42%, 15 min | 6.14 | 1.38 | 1 |
| 3:1 | 48%, 30 min | 5.25 | 1.08 | 1 |
| 3:1 | 57%, 1 h | 4.26 | 0.75 | 1 |
| 3:1 | 65%, 2 h | 3.62 | 0.54 | 1 |
| 3:1 | 66%, 6.5 h | 3.55 | 0.52 | 1 |
| 2:1 | 34%, 30 min | 4.88 | 1.94 | 1 |
| 2:1 | 43%, 1 h | 3.65 | 1.33 | 1 |
| 2:1 | 57%, 4 h | 2.51 | 0.75 | 1 |
| 1:1 | 34%, 2 h | 1.94 | 1.94 | 1 |
| 1:1 | 43%, 6.5 h | 1.33 | 1.33 | 1 |
| 1:2 | 40%, 1 h | 1.5 | 4 | 1 |
| 1:2 | 49%, 2 h | 1.04 | 3.08 | 1 |
| 1:2 | 55%, 3 h | 0.82 | 2.64 | 1 |
| 1:2 | 60%, 9 h | 0.67 | 2.33 | 1 |
| 1:3 | 39%, 15 min | 1.56 | 6.69 | 1 |
| 1:3 | 53%, 1 h | 0.89 | 4.66 | 1 |
| 1:3 | 62%, 2 h | 0.61 | 3.84 | 1 |
| 1:3 | 69%, 6.5 h | 0.45 | 3.35 | 1 |

Example 3

3-FL+LNnT ⇌ LNFP-III+Lac

The test was run in sodium phosphate buffer (50 mM, pH=6.5, 37° C., 200 μl), [3-FL]=200 mM, [LNnT]=200 mM. HPLC conditions: TSK Gel amide 80 (Tosoh, 3 μm, 150×4.6 mm) was used with a flow of 1 ml/min using 56% acetonitrile and 44% water. The elution of substrates and products was detected by CAD and/or UV detection at 195 nm.

The table below shows the composition of mixtures obtained for an enzyme extract of 2 mg/ml. Lactose is equimolar to LNFP-III.

| mutant | conversion time | molar ratio | | |
|---|---|---|---|---|
| | | 3-FL | LNnT | LNFP-III |
| N216D | 29.73%, 15 min | 2.36 | 2.36 | 1 |
| V221A | 24.19%, 15 min | 3.13 | 3.13 | 1 |
| V282K | 38.1%, 1 h | 1.62 | 1.62 | 1 |
| P134A | 40.46%, 15 min | 1.47 | 1.47 | 1 |

-continued

|  | | molar ratio | | |
|---|---|---|---|---|
| mutant | conversion time | 3-FL | LNnT | LNFP-III |
| W135F | 44.57%, 1 h | 1.24 | 1.24 | 1 |
| W135A | 45.58%, 15 min | 1.19 | 1.19 | 1 |
| W135E | 44.19%, 1 h | 1.26 | 1.26 | 1 |
| W170F | 40.06%, 15 min | 1.50 | 1.50 | 1 |
| A174S | 38.4%, 15 min | 1.60 | 1.60 | 1 |
| A174H | 49.3%, 2 h | 1.03 | 1.03 | 1 |

The table below shows the composition of mixtures obtained for an enzyme extract of 0.5 mg/ml. Lactose is equimolar to LNFP-III.

|  | | molar ratio | | |
|---|---|---|---|---|
| mutant | conversion time | 3-FL | LNnT | LNFP-III |
| N216D | 29.00%, 15 min | 2.45 | 2.45 | 1 |
| V221A | 26.00%, 15 min | 2.85 | 2.85 | 1 |
| V282K | 27.00%, 4 h | 2.70 | 2.70 | 1 |
| P134A | 32.00%, 1 h | 2.13 | 2.13 | 1 |
| W135F | 34.20%, 4 h | 1.92 | 1.92 | 1 |
| W135A | 36.00%, 2 h | 1.78 | 1.78 | 1 |
| W135E | 36.30%, 4 h | 1.75 | 1.75 | 1 |
| W170F | 32.00%, 2 h | 2.13 | 2.13 | 1 |
| A174S | 27.30%, 2 h | 2.66 | 2.66 | 1 |
| A174H | 44.00%, 6.5 h | 1.27 | 1.27 | 1 |
| Q244K | 22.50%, 15 min | 3.44 | 3.44 | 1 |

Example 4

The same test was carried out as in Example 3 using multi-point mutants. The table below shows the composition of mixtures obtained for an enzyme extract of 0.5 mg/ml. Lactose is equimolar to LNFP-III.

|  | | molar ratio | | |
|---|---|---|---|---|
| mutant | conversion time | 3-FL | LNnT | LNFP-III |
| S168E-A174H-E413R | 51.15%, 23 h | 0.96 | 0.96 | 1 |
| S168E-A174F | 49.16, 23 h | 1.03 | 1.03 | 1 |
| S168E-A174H-V282E | 51.55%, 6 h | 0.94 | 0.94 | 1 |
| S168E-A174H-V221A | 51.0%, 23 h | 0.96 | 0.96 | 1 |
| S168E-A174H-V221A-V282H | 51.08%, 6 h | 0.96 | 0.96 | 1 |
| W135E-A174F-V221A | 52.77%, 23 h | 0.90 | 0.90 | 1 |
| S168E-A174F-V221A-V282R | 52.12%, 23 h | 0.92 | 0.92 | 1 |
| S168E-A174H-N216D | 51.65%, 23 h | 0.94 | 0.94 | 1 |
| W135E-A174F-N216D-V221A | 50.01%, 6 h | 1 | 1 | 1 |
| S168E-A174H | 51.08%, 23 h | 0.96 | 0.96 | 1 |

Example 5

3-FL+LNFP-I  LNDFH-I+Lac

The test was run in sodium phosphate buffer (50 mM, pH=6.5, 37° C., 200 μl), [3-FL]=200 mM, [LNFP-1]=200 mM, enzyme extract=0.5 mg/ml. HPLC conditions: TSK Gel amide 80 (Tosoh, 3 μm, 150×4.6 mm) was used with a flow of 1 ml/min using 56% acetonitrile and 44% water. The elution of substrates and products was detected by CAD and/or UV detection at 195 nm.

The following table below shows the composition of mixtures obtained. Lactose is equimolar to LNDFH-I.

|  | | molar ratio | | |
|---|---|---|---|---|
| mutant | conversion time | 3-FL | LNFP-I | LNDFH-I |
| N216D | 43.3%, 15 min | 1.31 | 1.31 | 1 |
| V221A | 35.5%, 15 min | 1.82 | 1.82 | 1 |
| V282K | 36.8%, 25 h | 1.72 | 1.72 | 1 |
| P134A | 45.3%, 2 h | 1.21 | 1.21 | 1 |
| W135F | 51.9%, 25 h | 0.93 | 0.93 | 1 |
| W135A | 44.3%, 6.5 h | 1.26 | 1.26 | 1 |
| W135E | 50.7%, 25 h | 0.97 | 0.97 | 1 |
| W170F | 44.5%, 1 h | 1.25 | 1.25 | 1 |
| A174S | 31.7%, 25 h | 2.15 | 2.15 | 1 |
| Q244K | 42.8%, 15 min | 1.34 | 1.34 | 1 |
| S168E-A174F | 25.72%, 23 h | 2.89 | 2.89 | 1 |
| S168E-A174H-V221A | 24.75%, 23 h | 3.04 | 3.04 | 1 |
| W135E-A174F-V221A | 41.21%, 23 h | 1.43 | 1.43 | 1 |
| W135E-A174F-N2126D-V221A | 38.46%, 23 h | 1.60 | 1.60 | 1 |

Another test was run in sodium phosphate buffer (50 mM, pH=6.5, 30° C., 140 μl), [3-FL]=50 mM, [LNFP-1]=50 mM, enzyme extract=10 μl.

The following table below shows the composition of mixtures obtained. Lactose is equimolar to LNDFH-I.

|  | | molar ratio | | |
|---|---|---|---|---|
| mutant | conversion, time | 3-FL | LNFP-I | LNDFH-I |
| P134A | 33%, 15 min | 2.03 | 2.03 | 1 |
| P134V | 20%, 15 min | 4.0 | 4.0 | 1 |
| W135F | 37%, 4.5 h | 1.70 | 1.70 | 1 |
| W135A | 25%, 4.5 h | 3.0 | 3.0 | 1 |
| W135E | 37%, 4.5 h | 1.70 | 1.70 | 1 |
| W170F | 33%, 15 min | 2.03 | 2.03 | 1 |
| A236D | 38%, 15 min | 1.63 | 1.63 | 1 |
| A236H | 39%, 15 min | 1.56 | 1.56 | 1 |
| E237N | 38%, 4.5 h | 1.63 | 1.63 | 1 |
| Q244L | 42%, 15 min | 1.38 | 1.38 | 1 |
| Q244H | 42%, 15 min | 1.38 | 1.38 | 1 |
| Q244K | 41%, 15 min | 1.44 | 1.44 | 1 |
| Q244R | 31%, 15 min | 2.23 | 2.23 | 1 |
| Q245E | 36%, 15 min | 1.78 | 1.78 | 1 |
| W135E-A174F-A236E | 50%, 4.5 h | 1.00 | 1.00 | 1 |
| W135E-A174F-L238A | 51%, 4.5 h | 0.96 | 0.96 | 1 |
| W135E-A174F-T239H | 53%, 4.5 h | 0.89 | 0.89 | 1 |
| W135E-A174F-E241H | 52%, 4.5 h | 0.92 | 0.92 | 1 |

Example 6

The same test was carried out as in Example 5 in sodium phosphate buffer (50 mM, pH=6.5, 37° C. 150 μl), [3-FL]=100 mM, [LNFP-I]=50 mM, enzyme extract=10 μl crude extract. HPLC was as in Example 5.

The following table below shows the composition of mixtures obtained after 220 minutes. Lactose is equimolar to LNDFH-I.

|  | | molar ratio | | |
|---|---|---|---|---|
| mutant | conversion | 3-FL | LNFP-I | LNDFH-I |
| W135E-A174F-E413R | 40%, | 4.0 | 1.5 | 1 |
| W135Y-A174V-E413R | 45% | 3.44 | 1.22 | 1 |
| W135F-A174F-E413R | 41% | 3.88 | 1.44 | 1 |
| W135Y-A174F-E413R | 52% | 2.85 | 0.92 | 1 |
| W135Y-A174G-E413R | 43% | 3.65 | 1.33 | 1 |
| W135F-A174N-E413R | 58% | 2.45 | 0.72 | 1 |
| W135Y-A174N-E413R | 57% | 2.51 | 0.75 | 1 |

| mutant | conversion | molar ratio | | |
|---|---|---|---|---|
| | | 3-FL | LNFP-I | LNDFH-I |
| W135Q-A174N-E413R | 56% | 2.57 | 0.79 | 1 |
| W135Y-A174S-E413R | 47% | 3.26 | 1.13 | 1 |
| W135F-A174S-E413R | 52% | 2.85 | 0.92 | 1 |

Example 7

3-FL+2'-FL ⇌ DFL+Lac 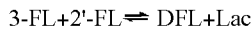

The test was run in sodium phosphate buffer (50 mM, pH=6.5, 37° C., 200 μl), [3-FL]=200 mM, [2'-FL]=200 mM, enzyme extract=0.5 mg/ml. HPLC conditions: TSK Gel amide 80 (Tosoh, 3 μm, 150×4.6 mm) was used with a flow of 1 ml/min using 56% acetonitrile and 44% water. The elution of substrates and products was detected by CAD and/or UV detection at 195 nm.

The table below shows the composition of mixtures obtained. Lactose is equimolar to DFL.

| mutant | conversion, time | molar ratio | | |
|---|---|---|---|---|
| | | 3-FL | 2'-FL | DFL |
| N216D | 46%, 30 min | 1.17 | 1.17 | 1 |
| V282K | 51%, 25 h | 0.96 | 0.96 | 1 |
| P134A | 54%, 2 h | 0.85 | 0.85 | 1 |
| W135F | 59%, 25 h | 0.69 | 0.69 | 1 |
| W135A | 52%, 6 h | 0.92 | 0.92 | 1 |
| W135E | 59%, 25 h | 0.69 | 0.69 | 1 |
| A174S | 41%, 4 h | 1.44 | 1.44 | 1 |
| A174H | 30%, 25 H | 2.33 | 2.33 | 1 |
| Q244K | 33%, 30 min | 2.03 | 2.03 | 1 |

Example 8

DFL+LNT ⇌ LNFP-I1+2'-FL 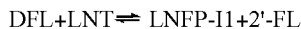

The test was run in sodium phosphate buffer (50 mM, pH=6.5, 37° C., 200 μl), using the W135F-A174N-N274A-E413R mutant, [DFL]=200 mM, [LNT]=200 mM, enzyme extract=0.1 or 0.25 mg/ml. HPLC conditions: TSK Gel amide 80 (Tosoh, 3 μm, 150×4.6 mm) was used with a flow of 1.1 ml/min using 66% acetonitrile and 34% water. The elution of substrates and products was detected by CAD and/or UV detection at 195 nm.

The tables below show the composition of mixtures obtained.

| enzyme extract: 0.1 mg/ml | | | | | |
|---|---|---|---|---|---|
| time (h) | LNFP-II conversion | DFL (mol %) | LNT (mol %) | LNFP-II (mol %) | 2'-FL (mol %) |
| 1 | 10% | 45% | 45% | 5% | 5% |
| 2 | 15% | 42.5% | 42.5% | 7.5% | 7.5% |
| 5 | 24% | 38% | 38% | 12% | 12% |
| 8 | 27% | 36.5% | 36.5% | 13.5% | 13.5% |

| enzyme extract: 0.25 mg/ml | | | | | |
|---|---|---|---|---|---|
| time (h) | LNFP-II conversion | DFL (mol %) | LNT (mol %) | LNFP-II (mol %) | 2'-FL (mol %) |
| 0.5 | 10% | 45% | 45% | 5% | 5% |
| 1 | 16% | 42% | 42% | 8% | 8% |
| 2 | 20% | 40% | 40% | 10% | 10% |
| 5 | 28% | 36% | 36% | 14% | 14% |
| 8 | 28% | 36% | 36% | 14% | 14% |

Example 9

DFL+LNnT ⇌ LNFP-III+2'-FL 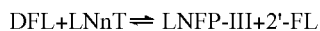

The test was run in sodium phosphate buffer (50 mM, pH=6.5, 37° C., 200 μl), using the W135F-A174N-N274A-E413R mutant, [DFL]=200 mM, [LNnT]=200 mM, enzyme extract=0.1 or 0.25 mg/ml. HPLC conditions: TSK Gel amide 80 (Tosoh, 3 μm, 150×4.6 mm) was used with a flow of 1.1 ml/min using 66% acetonitrile and 34% water. The elution of substrates and products was detected by CAD and/or UV detection at 195 nm.

The tables below show the composition of mixtures obtained.

| enzyme extract: 0.1 mg/ml | | | | | |
|---|---|---|---|---|---|
| time (h) | LNFP-III conversion | DFL (mol %) | LNnT (mol %) | LNFP-III (mol %) | 2'-FL (mol %) |
| 1 | 7% | 46.5% | 46.5% | 3.5% | 3.5% |
| 2 | 11% | 44.5% | 44.5% | 5.5% | 5.5% |
| 5 | 19% | 40.5% | 40.5% | 9.5% | 9.5% |
| 8 | 21% | 39.5% | 39.5% | 10.5% | 10.5% |

| enzyme extract: 0.25 mg/ml | | | | | |
|---|---|---|---|---|---|
| time (h) | LNFP-III conversion | DFL (mol %) | LNnT (mol %) | LNFP-III (mol %) | 2'-FL (mol %) |
| 0.5 | 8% | 46% | 46% | 4% | 4% |
| 1 | 12% | 44% | 44% | 6% | 6% |
| 2 | 17% | 41.5% | 41.5% | 8.5% | 8.5% |
| 5 | 24% | 38% | 38% | 12% | 12% |
| 8 | 25% | 37.5% | 37.5% | 12.5% | 12.5% |

Example 10

DFL+LNFP-I ⇌ LNDFH-I+2'-FL 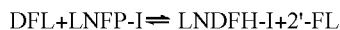

The test was run in sodium phosphate buffer (50 mM, pH=6.5, 37° C., 200 μl), using the W135F-A174N-N274A-E413R mutant, [DFL]=200 mM, [LNFP-I]=200 mM, enzyme extract=0.1 or 0.25 mg/ml. HPLC conditions: TSK Gel amide 80 (Tosoh, 3 μm, 150×4.6 mm) was used with a flow of 1.1 ml/min using 66% acetonitrile and 34% water. The elution of substrates and products was detected by CAD and/or UV detection at 195 nm.

The tables below show the composition of mixtures obtained.

| enzyme extract: 0.1 mg/ml | | | | | |
|---|---|---|---|---|---|
| time (h) | LNDFH-I conversion | DFL (mol %) | LNFP-I (mol %) | LNDFH-I (mol %) | 2'-FL (mol %) |
| 1 | 11% | 44.5% | 44.5% | 5.5% | 5.5% |
| 2 | 16% | 42% | 42% | 8% | 8% |
| 5 | 23% | 38.5% | 38.5% | 11.5% | 11.5% |
| 8 | 32% | 34% | 34% | 16% | 16% |

| enzyme extract: 0.25 mg/ml | | | | | |
|---|---|---|---|---|---|
| time (h) | LNDFH-I conversion | DFL (mol %) | LNFP-I (mol %) | LNDFH-I (mol %) | 2'-FL (mol %) |
| 0.5 | 11% | 44.5% | 44.5% | 5.5% | 5.5% |
| 1 | 20% | 40% | 40% | 10% | 10% |
| 2 | 28% | 36% | 36% | 14% | 14% |
| 5 | 36% | 32% | 32% | 18% | 18% |
| 8 | 38% | 31% | 31% | 19% | 19% |

Example 11

A total of 80 male and female patients are recruited to participate in the study. After a screening visit and run-in period of 1-2 weeks, the patients are selected and randomized into eight groups, each of 10 patients. Seven groups are each administered a treatment product containing 5 grams of one of the following compositions:
 i) LNT, 3-FL and LNFP-II,
 ii) LNnT, 3-FL and LNFP-III,
 iii) LNFP-I, 3-FL and LNDFH-I,
 iv) 3-FL, 2'-FL and DFL,
 v) 2'-FL, DFL, LNT and LNFP-II,
 vi) 2'-FL, DFL, LNnT and LNFP-III, or
 vii) 2'-FL, DFL, LNFP-I and LNDFH-I,
and one group the placebo product (2 grams of glucose) for 8 weeks. The treatment products and the placebo are in powder form in a unit dosage container.

The patients are eligible to participate if they are at least 18 years of age. All recruited patients are able and willing to understand and comply with the study procedures. Patients are excluded if: they have participated in a clinical study one month prior to screening visit; they have abnormal results in the screening tests which are clinically relevant for study participation; they are suffering for a severe disease such as malignancy, diabetes, severe coronary disease, kidney disease, neurological disease, or severe psychiatric disease or any condition which can confound the results of the study; used highly dosed probiotic supplements (yoghurt allowed) for 3 months prior to the study; consumed antibiotic drugs 3 months prior to the study; consumed on a regular basis any medication that might interfere with symptom evaluation 2 weeks prior to the study; and pregnant or lactating.

At the screening visit, medical history and concomitant medication is registered and a blood sample for safety analyses is collected. A faecal sample kit is distributed. Patients are instructed to keep their samples in the freezer until the next visit.

At the second visit, eligibility criteria are checked and eligible subjects are randomised to the three arms in the trial. The faecal samples are collected and equipment for new samples are distributed. Patients are familiarised with an interactive internet enabled system which records data daily and are provided with either treatment or control products. Subjects are reminded not to change their usual diet during the study. Blood samples are collected for biomarker studies. The faecal samples are stored at −80° C. until analysis. Faecal samples are subjected to 16 S RNA sequencing analysis.

The study runs for 8 weeks with the patients consuming either a placebo or a treatment product daily. Patients are instructed to consume the products in the morning with breakfast. Compliance is monitored through the interactive internet enabled system. The patients also use the system to record:
 Bristol Stool Form Scale (BSF) information,
 symptom information such as abdominal pain, abdominal discomfort, abdominal cramping, abdominal bloating, and abdominal fullness,
 additional Gastrointestinal Symptom Rating Scale (GSRS) information.

This questionnaire includes 15 items covering five dimensions (abdominal pain, indigestion, reflux, diarrhea, constipation) and uses a seven-graded Likert scale.

At the end of the study, each patient has an exit visit with the medical team. Faecal samples and blood samples are collected and analysed as before.

The faecal analysis indicates that the treatment patients have increased abundance of *Bifidobacterium* and *Bamesiella*, and reduced abundance of *Firmicutes*; especially *Clostridia*.

Example 12

Eighty 7-week-old C57BL/6J female mice are individually housed to avoid contamination between mice and provided with irradiated food and water. The mice are separated into 8 groups of 10 mice, 7 treatment groups and a placebo group.

The mice are treated with ampicillin (0.5 g/liter) in their drinking water, which is changed every 3 days. After 1 week, the ampicillin addition to the drinking water is terminated. Thereafter one of the following compositions:
 i) LNT, 3-FL and LNFP-II
 ii) LNnT, 3-FL and LNFP-III,
 iii) LNFP-I, 3-FL and LNDFH-I,
 iv) 3-FL, 2'-FL and DFL,
 v) 2'-FL, DFL, LNT and LNFP-II,
 vi) 2'-FL, DFL, LNnT and LNFP-III, or
 vii) 2'-FL, DFL, LNFP-I and LNDFH-I,
is added to the drinking water of each of the seven treatment groups at a total concentration of 40 mg/ml. The control group receives plain water. Fresh water is administered daily and all mice have free access to the drinking water. The mice are fed a rodent chow and are given fresh chow daily.

Two days after termination of the ampicillin treatment, mice of each group is infected by means of oral gavage with a vancomycin-resistant *Enterococcus faecium* strain (VRE). VRE levels are determined at different time points by plating serial dilutions of faecal pellets on Enterococcosel agar plates with vancomycin. VRE colonies are identified by appearance and confirmed by Gram staining. PCR of the vanA gene, which confers resistance to vancomycin, is used to confirm the presence of VRE in infected mice.

The mice are monitored for 2 weeks and are then euthanized. Fresh stool pellets are obtained before the mice are euthanized. The samples are immediately frozen and stored at −80° C. DNA is extracted using a 96-well PowerSoil DNA Isolation Kit (MO-BIO). A minimum of one sample-well per plate is kept empty to serve as a negative control during PCR. PCR is done with the forward primer S-D-Bact-0341-b-S-17 and reverse primer S-D-Bact-0785-a-A-

21 (Klindworth et al. Nucleic Acids Res. 41, e1 (2013)) with Illumina adapters attached. These are universal bacterial 16S rDNA primers, which target the V3-V4 region. The following PCR program is used: 98° C. for 30 sec, 25× (98° C. for 10 s, 55° C. for 20 s, 72° C. for 20 s), 72° C. for 5 min. Amplification is verified by running the products on a 1% agarose gel. Barcodes are added in a nested PCR using the Nextera Index Kit V2 (Illumina) with the following PCR program: 98° C. for 30 sec, 8× (98° C. for 10 s, 55° C. for 20 s, 72° C. for 20 s), 72° C. for 5 min. Attachment of primers is verified by running the products on a 1 agarose gel.

Products from the nested PCR are normalized using the SequalPrep Normalization Plate Kit and pooled. Pooled libraries are concentrated by evaporation and the DNA concentration of pooled libraries wisas measured on a Qubit fluorometer using the Qubit High Sensitivity Assay Kit (Thermo Fisher Scientific). Sequencing is done on a MiSeq desktop sequencer using the MiSeq Reagent Kit V3 (Illumina) for 2×300 bp paired-end sequencing. The 64-bit version of USEARCH (Edgar, 2013) is used for bioinformatical analysis of the sequence data.

In the HMO treated mice, VRE colonisation is reduced to undetectable levels within 14 days. The density of VRE reduces within 5 days. The untreated mice continue to harbour large numbers of VRE in the colon. The treatment groups of mice also show an abundance of *Porphyromonadaceae*, especially *Barnesiella*.

The invention claimed is:

1. A mixture of human milk oligosaccharides (HMOs) consisting essentially of: (a) 3-fucosyllactose, lacto-N-fucopentaose I, lacto-N-difucohexaose I and, optionally, lactose; or (b) difucosyllactose, 2'-fucosyllactose, and (i) lacto-N-tetraose and lacto-N-fucopentaose II, wherein the molar ratio of difucosyllactose to lacto-N-tetraose ranges from 2.5 to 5, (ii) lacto-N-neotetraose and lacto-N-fucopentaose III, wherein the molar ratio of difucosyllactose to lacto-N-neotetraose ranges from 2.5 to 5, or (iii) lacto-N-fucopentaose I and lacto-N-difucohexaose I.

2. The mixture of HMOs of claim 1, wherein the mixture consists essentially of 3-fucosyllactose, lacto-N-fucopentaose I, lacto-N-difucohexaose I, and, optionally, lactose, and wherein the molar ratio of (3-fucosyllactose+lacto-N-fucopentaose I) to lacto-N-difucohexaose I ranges from 0.8 to 9.50.

3. The mixture of HMOs of claim 2, wherein the molar ratio of 3-fucosyllactose to lacto-N-difucohexaose I or the molar ratio of lacto-N-fucopentaose I to lacto-N-difucohexaose I is not more than 2.

4. The mixture of HMOs of claim 2, wherein the molar ratio of 3-fucosyllactose to lacto-N-fucopentaose I ranges from 0.07 to 7.7.

5. The mixture of HMOs of claim 2, wherein the mixture consists essentially of 3-fucosyllactose, lacto-N-fucopentaose I, lacto-N-difucohexaose I and lactose, and wherein the molar ratio of lactose to lacto-N-difucohexaose I is about 1.

6. The mixture of HMOs of claim 1, wherein the mixture consists essentially of difucosyllactose, 2'-fucosyllactose, and (i) lacto-N-tetraose and lacto-N-fucopentaose II,
(ii) lacto-N-neotetraose and lacto-N-fucopentaose III, or
(iii) lacto-N-fucopentaose I and lacto-N-difucohexaose I.

7. The mixture of HMOs of claim 6, wherein the molar ratio of (difucosyllactose+lacto-N-tetraose) to lacto-N-fucopentaose II,
(difucosyllactose+lacto-N-neotetraose) to lacto-N-fucopentaose III, or
(difucosyllactose+lacto-N-fucopentaose I) to lacto-N-difucohexaose I
is 0.8-9.50.

8. The mixture of HMOs of claim 6, wherein the molar ratio of:
lacto-N-fucopentaose II to (difucosyllactose+lacto-N-tetraose),
lacto-N-fucopentaose III to (difucosyllactose+lacto-N-neotetraose), or
lacto-N-difucohexaose I to (difucosyllactose+lacto-N-fucopentaose I)
is at least 0.1.

9. A mixture of human milk oligosaccharides (HMOs) consisting essentially of 3-fucosyllactose and:
(a) lacto-N-tetraose, lacto-N-fucopentaose II and, optionally, lactose;
(b) lacto-N-neotetraose, lacto-N-fucopentaose III and, optionally, lactose; or
(c) 2'-fucosyllactose, difucosyllactose and lactose;
wherein the mixture is produced by a process comprising reacting 3-fucosyllactose and the lacto-N-tetraose, lacto-N-neotetraose, or 2'-fucosyllactose in a molar ratio of 0.2-5 in the presence of an α1-3/4 transfucosidase, and then removing the α1-3/4 transfucosidase and optionally the lactose from the reaction mixture, wherein the reaction has a conversion rate of at least 35%.

10. The mixture of HMOs of claim 9, wherein the mixture consists essentially of 3-fucosyllactose and:
   (a) lacto-N-tetraose and lacto-N-fucopentaose II, or
   (b) lacto-N-neotetraose and lacto-N-fucopentaose III.

11. The mixture of HMOs of claim 10, wherein the molar ratio of:
   (3-fucosyllactose+lacto-N-tetraose) to lacto-N-fucopentaose II, or
   (3-fucosyllactose+lacto-N-neotetraose) to lacto-N-fucopentaose III
is 0.8-9.50.

12. The mixture of HMOs of claim 11, wherein one of the molar ratios of:
   3-fucosyllactose to lacto-N-fucopentaose II and lacto-N-tetraose to lacto-N-fucopentaose II, or
   3-fucosyllactose to lacto-N-fucopentaose III and lacto-N-neotetraose to lacto-N-fucopentaose III
is not more than 2.

13. The mixture of HMOs of claim 10, wherein the molar ratio of the
   lacto-N-fucopentaose II to (3-fucosyllactose+lacto-N-tetraose), or
   lacto-N-fucopentaose III to (3-fucosyllactose+lacto-N-neotetraose)
is at least 0.1.

14. The mixture of HMOs of claim 10, wherein the molar ratio of 3-fucosyllactose to lacto-N-tetraose or lacto-N-neotetraose ranges from 0.05 to 21.

15. The mixture of HMOs of claim 9, wherein the mixture consists essentially of 3-fucosyllactose, lactose and:
   (i) lacto-N-tetraose and lacto-N-fucopentaose II,
   (ii) lacto-N-neotetraose and lacto-N-fucopentaose III, or
   (iii) 2'-fucosyllactose and difucosyllactose.

16. The mixture of HMOs of claim 15, wherein the molar ratio of
   (3-fucosyllactose+lacto-N-tetraose) to lacto-N-fucopentaose II,
   (3-fucosyllactose+lacto-N-neotetraose) to lacto-N-fucopentaose III, or
   (3-fucosyllactose+2'-fucosyllactose) to difucosyllactose
   ranges from 0.8 to 9.50; and wherein the molar ratio of lactose to lacto-N-fucopentaose II, lacto-N-fucopentaose III, or difucosyllatose is about 1.

17. The mixture of HMOs of claim 16, wherein the molar ratio of 3-fucosyllactose to lacto-N-fucopentaose II, lacto-N-fucopentaose III or difucosyllatose ranges from 0.07 to 7.7.

18. The mixture of HMOs of claim 16, wherein the molar ratio of 3-fucosyllactose to lactose or the molar ratio of
   lacto-N-tetraose to lacto-N-fucopentaose II,
   lacto-N-neotetraose to lacto-N-fucopentaose III, or
   2'-fucosyllactose and difucosyllactose
is not more than 2.

19. A method of preventing or treating bacterial infections in a human, the method comprising administering to the human a composition comprising a mixture of HMOs of claim 1.

20. A method of preventing or treating bacterial infections in a human, the method comprising administering to the human a composition comprising a mixture of HMOs of claim 9.

* * * * *